US006180341B1

(12) United States Patent
Iverson et al.

(10) Patent No.: US 6,180,341 B1
(45) Date of Patent: Jan. 30, 2001

(54) IN VITRO SCANNING SATURATION MUTAGENESIS OF PROTEINS

(75) Inventors: Brent L. Iverson; George Georgiou, both of Austin; Elizabeth A. Burks, Manchaca, all of TX (US)

(73) Assignee: Board of Regents, The Universiry of Texas System, Austin, TX (US)

( * ) Notice: Under 35 U.S.C. 154(b), the term of this patent shall be extended for 0 days.

(21) Appl. No.: 09/070,408

(22) Filed: Apr. 30, 1998

Related U.S. Application Data

(60) Provisional application No. 60/045,409, filed on May 1, 1997.

(51) Int. Cl.[7] .................................................. C12Q 1/68

(52) U.S. Cl. ............................................................ 435/6

(58) Field of Search .................................... 435/6

(56) References Cited

U.S. PATENT DOCUMENTS

| Re. 34,606 | 5/1994 | Estell et al. ............................ 435/222 |
|---|---|---|
| 4,034,074 | 7/1977 | Miles ...................................... 424/1 |
| 4,166,767 | 9/1979 | Kurooka et al. ......................... 435/7 |
| 4,496,658 | 1/1985 | Kondo et al. .......................... 436/516 |
| 4,748,119 | 5/1988 | Rich et al. ......................... 435/172.3 |
| 4,760,025 | 7/1988 | Estell et al. ........................... 435/222 |
| 4,873,192 | 10/1989 | Kunkel .............................. 435/172.3 |
| 4,959,312 | 9/1990 | Sirotkin ................................. 435/91 |
| 5,093,240 | 3/1992 | Inouye et al. ........................ 435/69.1 |
| 5,223,409 | 6/1993 | Ladner et al. ....................... 435/69.7 |
| 5,348,867 | 9/1994 | Georgiou et al. .................... 435/69.7 |
| 5,441,882 | 8/1995 | Estell et al. ........................... 435/222 |
| 5,723,323 | 3/1998 | Kauffman et al. ................. 435/272.3 |
| 5,733,541 | 3/1998 | Taichman et al. .................... 424/93.1 |
| 5,763,192 | 6/1998 | Kauffman et al. .................... 435/7.5 |

FOREIGN PATENT DOCUMENTS 0285123   10/1988  (EP).

OTHER PUBLICATIONS

Aiyar and Leis, "Modification of the Megaprimer Method of PCR Mutagenesis: Improved Amplification of the Final Product," *BioTechniques*, 14(3):366, 1993.
Amaravadi and King, "A rapid and efficient, nonradioactivemethod for screening recombinant DNA libraries," *BioTech.*, 16(1):98–103, 1994.
Barbas and Lerner, "Combinatorial Immunoglobulin libraries on the surface of phage (Phabs): Rapid selection of antigen–specificfabs," *Methods: A companion to Methods in Enzymology*, 2(2):119–124, 1991.
Barbas III et al., "Assembly of combinatorialantibody libraries on phage surfaces: The gene III site," *Proc. Natl. Acad. Sci. USA*, 88:7978–7982, Sep. 1991.
Barbas III et al., "Semisynthetic combinatorial antibody libraries: A chemical solution to the diversity problem," *Proc. Natl. Acad. Sci. USA*, 89:4457–4461,May 1992.

Barbas, "Recent advances in phage display," *Curr. Opin. BioTech.*, 4(5)526–530, 1993.
Bathurst, "Protein expression in yeast as an approach to production of recombinant malaria antigens," *Am. J. Trop. Med. Hyg.*, 50(4 Suppl):20–26, 1994.
Beher, "Correlation between the expression of an *Escherichia coli* cell surface protein and the ability of the protein to bind to lipopolysaccharide," *J. Bacteriol.*, 143(1):403–410, 1980.
Bender et al., "Recombinant human antibodies: linkage of an Fab fragment from a combinatorial library to an Fc fragment for expression in mammalian cell culture," *Hum. Antibodies Hybridomas*, 4(2):74–79, 1993.
Better et al., "*Escherichia coli* Secretion of an Active Chimeric Antibody Fragment," *Science*, 240:1041–1043, May 1988.
Bird et al., "Single–chain antigen–binding proteins," *Science*, 242:423–426, 1988.
Blackburn et al., "Electrochemiluminescence detection for development of immunoassays and DNA probe assays for clinical diagnostics," *Clinical Chemistry*, 37(9):1534–1539, 1991.
Boder and Wittrup, "Yeast surface display for screening combinatorial polypeptide libraries," *Nat. Biotechnol.*, 15(6):553–557, 1997.
Boss et al., "Assembly of functional antibodies from immunoglobulin heavy and light chains synthesised in *E. coli*," *Nucl. Acids Res.*, 12(9):3791–3807, 1984.
Breyer and Sauer, "Mutational analysis of the fine specificity of binding of monoclonal antibody 51F to λ repressor," *J. Biol. Chem.*, 264(22):13355–13360, 1989.
Buckholz, "Yeast systems for the expression of heterologous gene products," *Curr. Opin. Biotechnol.*, 4(5):538–542, 1993.
Buell et al., "Optimizing the expression in *E. coli* of a synthetic gene encoding somatomedin–C (IGF–I), " *Nucl. Acids Res.*, 13(6), 1923–1938, 1985.
Cabilly et al., "Generation of antibody from immunoglobulinpolypeptide chains produced in *E. coli*," *Proc. Natl. Acad. Sci. USA*, 81:3273–3277, 1984.

(List continued on next page.)

*Primary Examiner*—Charles L. Patterson, Jr.
(74) *Attorney, Agent, or Firm*—Fulbright & Jaworski LLP

(57) ABSTRACT

The present invention combines PCR™ mutagenesis with in vitro transcription/translation and ELISA for the rapid generation and characterization of protein mutants. The PCR™ products are used directly as the template for the in vitro transcription/translation reactions and because no cloning steps are required, the in vitro saturation mutagenesis of one residue can be completed in duplicate within a week by a single investigator. This high throughput enables the saturation mutagenesis of numerous residues of interest, a process that can be described as in vitro scanning saturation mutagenesis. Compositions and methods of use of such a process are described herein.

21 Claims, 8 Drawing Sheets

OTHER PUBLICATIONS

Caton and Koprowski, "Influenza virus hemagglutinin–specific antibodies isolated from a combinatorial expression library are closely related to the immune response of the donor," *Proc. Natl. Acad. Sci. USA*, 87:6450–6454, 1990.

Chang et al., "Membrane biogenesis: Cotranslational integration of the bacteriophage f1 coat protein into an *E. Coli* membrane fraction," *Proc. Natl. Sci. USA*, 76:1251–1255, 1979.

Charbit et al., "Permissive sites and topology of an outer membrane protein with a reporter epitope," *J. Bact.*, 173(1):262–275, 1991.

Chen et al., "A quantitative immunoassay utilizing *E. coli* possessing surface–expressed single chain Fv molecules," *BioTech. Prog.*, 12:572–574, 1996.

Chiang et al., "Direct cDNA cloning of the rearranged immunoglobulin variable region," *BioTechniques*, 7(4):360–366, 1989.

Chiswell and McCafferty, "Phage antibodies: will new 'coliclonal' antibodies replace monoclonal antibodies?", *Tibtech*, 10:80–84, 1992.

Clackson et al., "Making antibody fragments using phage display libraries," *Nature*, 352:624–628, Aug. 1991.

Colizzie et al., "Analysis of Mycobacterium tuberculosis genoma and production of a recombinant protein containing specific B and T cell antigenic determinants—new approaches to second generation antituberculosis vaccines," *Z Erkr Atmungsorgane*, 172(1):40–52, 1989.

Cryz, "Live attenuated vaccines for human use," *Curr. Opin. BioTech.*, 3(3):298–302, 1992.

Danziger et al., "Simultaneous gene amplification and gene detection using three PCR primers," *BioTechniques*, 14(3):370, 1993.

Denzin et al., "Single–chain site–specific mutations of fluorescein–amino acid contact residues in high affinity monoclonal antibody 4–4–20," *J. Biol. Chem.*, 266(21):14095–14103, 1991.

Derbyshire et al., "A simple and efficient procedure for saturation mutagenesis using mixed oligodeoxynucleotides," *Gene*, 46:145–152, 1986.

Devlin et al., "Random peptide libraries: A source of specific protein binding molecules," *Science*, 249:404–406, 1990.

Dunn, "Phage display of proteins," *Curr. Opin. Biotechnol.*, 7(5):547–553, 1996.

Eckart and Bussineaus, "Quality and authenticity of heterologous proteins synthesized in yeast," *Curr. Opin. BioTech.*, 7(5):525–530, 1996.

Fischetti et al., "Expression of foreign proteins on gram–positive commensal bacteria for mucosal vaccine delivery," *Curr. Opin. Biotechnol.*, 4(5):603–610, 1993.

Francisco and Georgiou, "The expression of recombinant proteins on the external surface of *Escherichia coli*. Biotechnological applications," *Ann. NY Acad. Sci.*, 745:372–382, 1994.

Francisco et al., "Production and fluorescence–activated cell sorting of *Escherichia coli* expressing a functional antibody fragment on the external surface" *Proc. Natl. Acad. Sci. USA*, 90:10444–10448, Nov. 1993.

Francisco et al., Transport and anchoring of β–lactamase to the external surface of *Escherichia coli*, *Proc. Natl. Acad. Sci. USA*, 89:2713–2717, Apr. 1992.

Gellissen et al., "Heterologous protein production in yeast," *Antonie Van Leeuwenhoek*, 62(102):79–93, 1992.

Georgiou et al., "Folding and aggregation of β–lactamase: Analogies with the formation of inclusion bodies in *Escherichia coli*," *Protein Science*, 3:1953–1960, 1994.

Georgiou et al., "Display of heterologous proteins on the surface of microorganisms: from the screening of combinatorial libraries to live recombinant vaccines," *Nat. Biotechnol.*, 15(1):29–34, 1997.

Georgiou et al., "Practical applications of engineering gram–negative bacterial cell surfaces," *Trends BioTech.*, 11(1):6–10, 1993.

Goward et al., "Molecular evolution of bacterial cell–surface proteins," *Trends Biochem. Sci.*, 18(4):136–140, 1993.

Gram et al., "In vitro selection and affinity maturation of antibodies from a naive combinatorial immunoglobulin library," *Proc. Natl. Acad. Sci. USA*, 89(3576–3580, 1992.

Hansson et al., "Expression of recombinant proteins on the surface of the coagulase–negative bacteruim *Staphylococcus xylosus*," *J. Bacteriol.*, 174(13):4239–4245, 1992.

Hill et al., "Mutagenesis with degenerate oligonucleotides: an efficient method for saturating a defined DNA region with base pair substitutions," *Meth. Enzymol.*, 155:558–568, 1987.

Hill et al., "Saturation mutagenesis of the yeast his3 regulatory site: requirements for transcriptional induction and for binding by GCN4 activator protein," *Science*, 234:451–457, 1986.

Hockney, "Recent developments in heterologous protein production in *Escherichia coli*," *Trends Biotechnol.*, 12(11):456–463, 1994.

Huse et al., "Generation of a large combinatorial library of the immunoglobulin repertoire in phage lambda," *Science*, 246:1275–1281, 1989.

Huse, "Combinatorial antibody expression libraries in filamentous phage," In: *Antibody Engineering: A Practical Guide*, Borrebaeck (Ed.), pp. 103–120, 1992.

Huston et al., "Protein engineering of single–chain Fv analogs and fusion proteins," *Molecular Design and Modeling: Concepts and Applications Part B Antibodies and Antigens, Nucleic Acids, Polysaccharides, and Drugs, Methods in Enzymology*, Langone, Ed., Academic Press, Inc. San Diego 203:46–98, 1991.

Huston et al., Protein engineering of antibody binding sites: Recovery of specific activity in an anti–digoxin single–chain Fv analogue produced in *E. Coli*, *Proc. Natl. Acad. Sci. USA*, 85:5879–5883, 1998.

Hutchison et al., "A complete library of point substitution mutations in the glucocorticoid response element of mouse mammary tumor virus," *Proc. Natl. Acad. Sci. USA*, 83:710–714, 1986.

Ikeda et al., "A fusion protein library: an improved method for rapid screening and characterization of DNA binding or interacting proteins," *Gene*, 181(1–2):167–171, 1996.

Inouye et al., "Amino acid sequence for the peptide extension on the prolipoprotein of the *E. coli* outer membrane," *Proc. Natl. Acad. Sci. USA*, 74(3):1004–1008, 1977.

Irving et al., "Protein engineering: the selection of proteins with improved binding affintiy using complex expression libraries," *Australas Biotechnol.*, 3(2):86–93, 1993.

Ito et al., "A general method for introducing a series of mutations into cloned DNA using the polymerase chain reaction," *Gene*, 102:67–70, 1991.

Iverson et al., "A Combinatorial System for Cloning and Expressing the Catalytic Antibody Repertoire in *Escherichia coli*," *Cold Spring Harbor Symposia on Quantitative Biology*, vol. LIV., 273–280. 1989.

Iverson et al., Metalloantibodies, *Science*, 249:659–662, 1990.

Jonsson and Kronvall, "The use of protein A–containing *Staphylococcus aureus* as a solid phase anti–IgG reagent in radioimmunoassasyas exemplified in the quantitation of α–fetoprotein in normal human adult serum" *J. Eur. Immunol.*, 4:29–33, 1974.

Kang et al., "Linkage of recognition and replication functions by assembling combinatorial antibody Fab libraries along phage surfaces," *Proc. Natl. Acad. Sci. USA*, 88:4363–4366, 1991.

Kauffman, "Applied molecular evolution," *J. Theor. Biol.*, 157:1–7, 1992.

Kessler, "Rapid isolation of antigens from cells with a Staphylococcal protein A–antibody adsorbent: parameters of the interaction of antibody–antigencomplexes with Protein $A^1$," *J. Immunology*, 115(6):1617–1624,1975.

Kingsman and Kingsman, "Polyvalent recombinant antigens: a new vaccine strategy," *Vaccine*, 6(4):304–306, 1988.

Koths, "Recombinant proteins for medical use: the attractions and challenges," *Curr. Opin. Biotechnol.*, 6(6):681–687, 1995.

Kwoh et al., "Transcription–basedamplification system and detection of amplified human immunodeficiencyvirus type 1 with a bead–based sandwich hybridization format," *Proc. Natl. Acad. Sci. USA*, 86:1173–117. 1989.

LaBean and Kauffman, "Design of synthetic gene libraries encoding random sequence proteins with desired ensemble characteristics," *Protein Sci.*, 2:1249–1254, 1993.

LaBean et al., "Design, expression, and characterizationof random sequence polypeptides as fusions with ubiquitin," *FASEB*, 6(1):Abstract#2714, 1992.

Larrick et al., "Rapid cloning of rearranged immunoglobulin genes from human hybridoma cells using mixed primers and the polymerase chain reaction," *Biochem. BioPhys. Res. Comm.*, 160(3):1250–1256, 1989.

Lerner et al., "Antibodies without immunization," *Science*, 258:1313–1314, 1992.

Little et al., "Bacterial surface presentation of proteins and peptides: an alternative to phage technology," *Trends BioTech.*, 11(1):3–5, 1993.

Lugtenberg and van Alphen, "Molecular architecture and functioning of the outer membrane of *E. coli*, and other gram–negative bacteria," *Biochimica Biophysica A.*, 737:51–115, 1983.

Martin et al., "Surface baterial antigen CS31A as a tool to design new recombinant vaccines displaying heterologous antigenic determinants," *Vet. Res.*, 26(3):209–210, 1995.

Matteucci and Heyneker, "Targeted random mutagenesis: the use of ambiguously synthesized oligonucleotides to mutagenize sequences immediately 5' of an ATG initiation codon," *Nucl. Acids Res.*, 11(10):3113–3121, 1983.

McCafferty et al., "Phage antibodies: filamentous phage displaying antibody variable domains," *Nature*, 348:552–554, 1990.

McGregor, "Selection of proteins and peptides from libraries displayed on filamentous bacteriophage," *Mol. Biotechnol.*, 6(2):155–162, 1996.

McManus and Riechmann, "Use of 2D NMR, protein engineering, and molecular modeling to study the hapten–binding site of an antibody $F_v$ fragment against 2–phenyloxazolone," *Biochem.*, 30:5851–5857, 1991.

Morona et al., "*Escherichia coli* K–12 outer membrane protein (OmpA) as a bacteriophage receptor: Analysis of mutant genes expressing altered proteins," *J. Bacteriology*, 159(2):570–578, 1984.

Morrison and Desrosiers,"A PCR–based strategy for extensive mutagenesis of a target DNA sequence," *BioTech.*, 14(3):454–457, 1993.

Mullinax et al., "Identification of human antibody fragment clones specific for tetanus toxid in a bacteriophae λ immunoespression library," *Proc. Natl. Acad. Sci. USA*, 87:8095–8099, 1990.

Myers et al., "A general method for saturation mutagenesis of cloned DNA fragments," *Science*, 229:242–247, 1985.

Neuberger et al., "Recombinant antibodies possessing novel effector functions," *Nature*, 312:604–608, 1984.

Nguyen et al., "Cell–surface display of heterologous epitopes on *Staphylococcus xylosus* as a potential delivery system for oral vaccination," *Gene*, 128(1):89–94, 1993.

Nguyen et al., "Hydrophobicity engineering to facilitate surface display of heterologous gene products on *Staphylococcus xylosus,*" *J. Biotechnol.*, 42(3):207–219, 1995.

Nishiyama and Tokuda, "Dynamic structure change of protein secretion machinery," [article in Japanese], *Tanpakushitsu Kakusan Koso*, 42(1):1–11, 1997 (An English translation of the abstract is attached thereto).

O'Neil and Hoess, "Phage display: protein engineering by directed evolution," *Curr. Opin. Struct. Biol.*, 5(4):443–449, 1995.

Ohara et al., "One–sided polymerase chain reaction: the amplification of cDNA," *Proc. Natl. Acad. Sci. USA*, 86:5673–5677, 1989.

Oliphant and Struhl, "The use of random–sequence oligonucleotides for determining consensus sequences," *Meth. Enzymol.*, 155(35):568–583, 1987.

Oliphant et al., "Cloning of random–sequence oligodeoxynucleotides," *Gene*, 1662(44):177–183, 1986.

Orlandi et al., "Cloning immunoglobulin variable domains for expression by the polymerase chain reaction," *Proc. Natl. Acad. Sci. USA*, 86:3833–3837, 1989.

Parmley an Smith, "Antibody–selectable filamentous fd phage vectors: affinity purification of target genes," *Gene*, 73:305–318, 1988.

Persson et al., "Generation of diverse high–affinity human monoclonal antibodies by repertoire cloning," *Proc. Natl. Acad. Sci. USA*, 88:2432–2436, Mar. 1991.

Plückthun and Skerra, Expression of functional antibody Fv and Fab fragments in *E. coli*, *Meth. Enzym.*, 178:497–515, 1989.

Plückthun, "Antibodies from *E. coli,*" *Nature*, 347:497–498, 1990.

Posner et al., "Catalytic antibodies: perusing combinatorial libraries," *Trends Biochem. Sci.*, 19(4):145–150, 1994.

Reidhaar–Olson and Sauer, "Combinatorial cassette mutagenesis as a probe of the informational content of protein sequences," *Science*, 241:53–57, 1988.

Riechmann et al., "Reshaping human antibodies for therapy," *Nature*, 332:323–327, 1988.

Robert et al., "Surface display on staphylococci: a comparative study," *FEBS Lett.*, 390(3):327–333, 1996.

Roberts et al., "Affinity maturation of proteins displayed on surface of M13 bacteriophageas major coat protein fusions," *Meth. Enzy.*, 267:68–82, 1996.

Russell et al., "Production of recombinant products in yeasts: a review," *Aust. J. Biotechnol.*, 5(1):48–55, 1991.

Samuelson et al., "Cell surface display of recombinant proteins on *Staphylococcus carnosus*," *J. Bacteriol.*, 177(6):1470–1476, 1995.

Sastry et al., "Cloning of the immunological repertoire in *Escherichiacoli* for generation of monoclonal catalytic antibodies: Construction of a heavy chain variable region–specificcDNA library," *Proc. Natl. Acad. Sci. USA*, 86:5728–5732, Aug. 1989.

Sastry et al., "Screening combinatorialantibody libraries for catalytic acyl transfer reactions," *Ciba Found Symp.*, 159:145–151, 1991.

Schatz, "Construction and screening of biological peptide libraries," *Curr. Opin. BioTech.*, 5(5):487–494, 1994.

Schildbach et al., "Modulation of antibody affinity by a non–contact residue," *Protein Science*, 2:206–214, 1993.

Scott and Craig, "Random peptide libraries," *Curr. Opin. BioTech.*, 5(1):40–48, 1994.

Scott and Smith, Searching for peptide ligands with an epitope library, *Science*, 249:386–390, 1990.

Sepetov et al., "Library of libraries: approach to synthetic combinatorial library design and screening of 'pharmacophore' motifs," *Proc. Natl. Acad. Sci. USA*, 92(12):5426–5430, 1995.

Short et al., λ ZAP: a bacteriophage λ expression vector with in vivo excision properties, *Nucl. Acids Res.*, 16:7583–7600, 1988.

Skerra and Plückthun, Assembly of a functional immunoglobulin $F_v$ fragment in *E. coli*, *Science*, 240:1038–1041, 1988.

Smith, "Surface presentation of protein epitopes using bacteriophage expression systems," *Curr. Opin. Biotechnol.*, 2(5):668–673, 1991.

Stone et al., "Identification of functional regions in the transforming protein of Fujinami sarcoma virus by in–phase insertion mutagenesis," *Cell*, 37:549–558, 1984.

Sudberry, "The expression of recombinant proteins in yeasts," *Curr. Opin. Biotechnol.*, 7(5):517–524, 1996.

Vershon et al., "Mutagenesis of the arc repressor using synthetic primers with random nucleotide substitutions," *Protein Eng.*, 15:243–256, 1986.

Walker et al., Isothermal in vitro amplification of DNA by a restriction enzyme/DNA polymerase system, *Proc. Natl. Acad. Sci. USA*, 89:392–396, 1992.

Wang et al., "Use of a gene–targetedphage display random epitope library to map an antigenic determinant on the bluetongue virus outer capsid protein VP5," *J. Immunol. Methods*, 178(1):1–12, 1995.

Ward et al., "Binding activities of a repertoire of single immunoglobulin variable domains secreted from *E. coli*," *Nature*, 341:544–546, 1989.

Waye et al., "EcoK selection vectors for shotgun cloning into M13 and deletion mutagenesis," *Nucl. Acids Res.*, 13(23):8561–8571, 1985.

Wilcox and Studnicka, "Expression of foreign proteins in microorganisms," *Biotechnol. Appl. Biochem.*, 10(6):500–509, 1988.

Winter and Milstein, "Man–made antibodies," *Nature*, 349:293–299, 1991.

Wiseman, "The organization of production of genetically–engineered proteins in yeast," *Endeavour*, 16(4):190–193, 1992.

Wu and Wallace, "The ligation amplification reaction (LAR)–amplification of speicfic DNA sequences using sequential rounds of template–dependent ligation," *Genomics*, 4:560–569, 1989.

Yang et al., Electrochemiluminescence: A New Diagnostic and Research Tool, *Bio/Technology*, 12:193–194, Feb. 1994.

Yarranton, "Mammalian recombinant proteins: vectors and expression systems," *Curr. Opin. Biotechnol.*, 1(2):133–140, 1990.

Youderian et al., "Changing the DNA–binding specificity of a repressor," *Cell*, 35(Pt2):777–783, 1983.

Kunkel et al. (1985) Proc. Natl. Acad. Sci. USA 82:488–492, 1985.*

Renshaw–Gegg, L., et al. (1996) Biotech. Lett. 18(6), 679–682.*

Switzer, W. M., et al. (1995) Biotech. 18(2), 244–248.*

Henkel, T., et al. (1993) Anal. Biochem. 214, 351–352.*

Burks, E. A., et al. (1997) Proc. Natl. Acad. Sci., USA 94, 412–417.*

* cited by examiner

|  | $R_1$ | $R_2$ | $R_3$ | $R_4$ | $R_5$ | $R_6$ |
|---|---|---|---|---|---|---|
| Digoxin | Sugars | H | $CH_3$ | H | OH | H |
| Digitoxin | Sugars | H | $CH_3$ | H | H | H |
| Digoxigenin | H | H | $CH_3$ | H | OH | H |
| Ouabain | Sugars | OH | $CH_2OH$ | OH | H | OH |

Full-length gene with coding for transcription and translation

↓ In vitro transcription/translation mutant scFv(Dig)

↓ Antigen capture ELISA

↓ HO50

SEQUENCE LISTING (1) GENERAL INFORMATION:

(iii) NUMBER OF SEQUENCES: 132

(2) INFORMATION FOR SEQ ID NO:1:

(i) SEQUENCE CHARACTERISTICS:
      (A) LENGTH: 1010 base pairs
      (B) TYPE: nucleic acid
      (C) STRANDEDNESS: single
      (D) TOPOLOGY: linear (xi) SEQUENCE DESCRIPTION: SEQ ID NO:1:

```
CGATGCGTCC GGCGTAGAGG ATCGAGATCT CGATCCCGCG AAATTAATAC GACTCACTAT      60

AGGGGAATTG TGAGCGGATA ACAATTCCCC TCTAGAAATA ATTTTGTTTA ACTTTAAGAA     120

GGAGATATAC ATATGGAAGT TCAACTGCAA CAGTCTGGTC CTGAATTGGT TAAACCTGGC     180

GCCTCTGTGC GCATGTCCTG CAAATCCTCA GGGTACATTT TCACCGACTT CTACATGAAT     240

TGGGTTCGCC AGTCTCATGG TAAGTCTCTA GACTACATCG GGTACATTTC CCCATATTCT     300

GGGGTTACCG GCTACAACCA GAAGTTTAAA GGTAAGGCCA CCCTTACTGT CGACAAATCT     360

TCCTCAACTG CTTACATGGA GCTGCGTTCT TTGACCTCTG AGGACTCCGC GGTATACTAT     420
```

-continued

```
TGCGCCGGCT CCTCTGGTAA CAAATGGGCC ATGGATTATT GGGGTCATGG TGCTAGCGTT      480

ACTGTGAGCT CTGGTGGCGG TGGCTCGGGC GGTGGTGGGT CGGGTGGCGG CGGATCAGAC      540

ATAGTACTGA CCCAGTCTCC AGCTTCTTTG GCTGTGTCTC TAGGACAAAG GGCCACGATA      600

TCCTGCCGAT CCAGCCAAAG TCTCGTACAT TCTAATGGTA ATACTTATCT GAACTGGTAC      660

CAACAGAAAC CAGGACAGCC ACCCAAGCTT CTCATCTATA AGGTATCCAA CCGATTCTCT      720

GGAGTCCCTG CCAGGTTCAG TGGCAGTGGG TCTGAGTCAG ACTTCACCCT CACCATCGAT      780

CCTGTGGAGG AAGATGATGC TGCAATATAT TACTGTAGCC AAACTACGCA TGTTCCACCC      840

ACGTTCGGCT CGGGGACCAA GCTCGAGATC AAACGGGCTA GCCAGCCAGA ACTCGCCCCG      900

GAAGACCCCG AGGATGTCGA GCACCACCAC CACCACCACT GAGATCCGGC TGCTAACAAA      960

GCCCGAAAGG AAGCTGAGTT GGCTGCTGCC ACCGCTGAGC AATAACTAGC                1010
```

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:2:

```
CGGTGAAAAT GTACCCTG                                                     18
```

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:3:

```
CAGGGTACAT TTTCACCGAC TTCTACATGA ATTGGG                                 36
```

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:4:

```
CAGGGTACAT TTTCACCGAC TTCGCAATGA ATTGGG                                 36
```

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

```
CAGGGTACAT TTTCACCGAC TTCCGTATGA ATTGGG                                 36
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single (D) TOPOLOGY: linear (xi) SEQUENCE DESCRIPTION: SEQ ID NO:6:

CAGGGTACAT TTTCACCGAC TTCAACATGA ATTGGG                    36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:7:

CAGGGTACAT TTTCACCGAC TTCGACATGA ATTGGG                    36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:8:

CAGGGTACAT TTTCACCGAC TTCTGCATGA ATTGGG                    36

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:9:

CAGGGTACAT TTTCACCGAC TTCGAAATGA ATTGGG                    36

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:10:

CAGGGTACAT TTTCACCGAC TTCCAGATGA ATTGGG                    36

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:11:

CAGGGTACAT TTTCACCGAC TTCGGCATGA ATTGGG                    36

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:12:

CAGGGTACAT TTTCACCGAC TTCCACATGA ATTGGG                36

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:13:

CAGGGTACAT TTTCACCGAC TTCATCATGA ATTGGG                36

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

CAGGGTACAT TTTCACCGAC TTCCTGATGA ATTGGG                36

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:15:

CAGGGTACAT TTTCACCGAC TTCAAAATGA ATTGGG                36

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:16:

CAGGGTACAT TTTCACCGAC TTCATGATGA ATTGGG                36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

CAGGGTACAT TTTCACCGAC TTCTTCATGA ATTGGG                36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

CAGGGTACAT TTTCACCGAC TTCCCGATGA ATTGGG 36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

CAGGGTACAT TTTCACCGAC TTCTCCATGA ATTGGG 36

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:20:

CAGGGTACAT TTTCACCGAC TTCACCATGA ATTGGG 36

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:21:

CAGGGTACAT TTTCACCGAC TTCTGGATGA ATTGGG 36

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:22:

CAGGGTACAT TTTCACCGAC TTCGTTATGA ATTGGG 36

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:23:

CAGGGTACAT TTTCACCTGA TTCTGAATGA ATTGGG 36

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

GTAGAAGTCG GTGAAAATGT                                            20

(2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:25:

ACATTTTCAC CGACTTCTAC ATGGCATGGG TTCGC                           35

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:26:

ACATTTTCAC CGACTTCTAC ATGCGTTGGG TTCGC                           35

(2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:27:

ACATTTTCAC CGACTTCTAC ATGAACTGGG TTCGC                           35

(2) INFORMATION FOR SEQ ID NO:28:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:28:

ACATTTTCAC CGACTTCTAC ATGGACTGGG TTCGC                           35

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:29:

ACATTTTCAC CGACTTCTAC ATGTGCTGGG TTCGC                           35

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:30:

```
ACATTTTCAC CGACTTCTAC ATGGAATGGG TTCGC                                      35

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:31:

ACATTTTCAC CGACTTCTAC ATGCAGTGGG TTCGC                                      35

(2) INFORMATION FOR SEQ ID NO:32:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:32:

ACATTTTCAC CGACTTCTAC ATGGGCTGGG TTCGC                                      35

(2) INFORMATION FOR SEQ ID NO:33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:33:

ACATTTTCAC CGACTTCTAC ATGCACTGGG TTCGC                                      35

(2) INFORMATION FOR SEQ ID NO:34:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:34:

ACATTTTCAC CGACTTCTAC ATGATCTGGG TTCGC                                      35

(2) INFORMATION FOR SEQ ID NO:35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:35:

ACATTTTCAC CGACTTCTAC ATGCTGTGGG TTCGC                                      35

(2) INFORMATION FOR SEQ ID NO:36:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:36:

ACATTTTCAC CGACTTCTAC ATGAAATGGG TTCGC                                      35
```

(2) INFORMATION FOR SEQ ID NO:37:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:37:

ACATTTTCAC CGACTTCTAC ATGATGTGGG TTCGC                            35

(2) INFORMATION FOR SEQ ID NO:38:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:38:

ACATTTTCAC CGACTTCTAC ATGTTCTGGG TTCGC                            35

(2) INFORMATION FOR SEQ ID NO:39:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:39:

ACATTTTCAC CGACTTCTAC ATGCCGTGGG TTCGC                            35

(2) INFORMATION FOR SEQ ID NO:40:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:40:

ACATTTTCAC CGACTTCTAC ATGTCCTGGG TTCGC                            35

(2) INFORMATION FOR SEQ ID NO:41:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:41:

ACATTTTCAC CGACTTCTAC ATGACCTGGG TTCGC                            35

(2) INFORMATION FOR SEQ ID NO:42:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:42:

ACATTTTCAC CGACTTCTAC ATGTGGTGGG TTCGC                            35

(2) INFORMATION FOR SEQ ID NO:43:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:43:

ACATTTTCAC CGACTTCTAC ATGTACTGGG TTCGC                                        35

(2) INFORMATION FOR SEQ ID NO:44:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:44:

ACATTTTCAC CGACTTCTAC ATGGTTTGGG TTCGC                                        35

(2) INFORMATION FOR SEQ ID NO:45:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:45:

ACATTTTCAC CGACTTCTAC TGATGATGGG TTCGC                                        35

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:46:

TCCCCATATT CTGGGGTTAC                                                         20

(2) INFORMATION FOR SEQ ID NO:47:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:47:

AGCCGGTAAC CCCAGAATAT GGGGAAATGT ACCCGATGTA GTCTAG                            46

(2) INFORMATION FOR SEQ ID NO:48:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:48:

AGCCGGTAAC CCCAGAATAT GGGGAAATTG CCCCGATGTA GTCTAG                            46

(2) INFORMATION FOR SEQ ID NO:49:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:49:

AGCCGGTAAC CCCAGAATAT GGGGAAATAC GCCCGATGTA GTCTAG           46

(2) INFORMATION FOR SEQ ID NO:50:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:50:

AGCCGGTAAC CCCAGAATAT GGGGAAATGT TCCCGATGTA GTCTAG           46

(2) INFORMATION FOR SEQ ID NO:51:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:51:

AGCCGGTAAC CCCAGAATAT GGGGAAATGT CCCCGATGTA GTCTAG           46

(2) INFORMATION FOR SEQ ID NO:52:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:52:

AGCCGGTAAC CCCAGAATAT GGGGAAATGC ACCCGATGTA GTCTAG           46

(2) INFORMATION FOR SEQ ID NO:53:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:53:

AGCCGGTAAC CCCAGAATAT GGGGAAATTT CCCCGATGTA GTCTAG           46

(2) INFORMATION FOR SEQ ID NO:54:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:54:

AGCCGGTAAC CCCAGAATAT GGGGAAATCT GCCCGATGTA GTCTAG           46

(2) INFORMATION FOR SEQ ID NO:55:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (xi) SEQUENCE DESCRIPTION: SEQ ID NO:55:

AGCCGGTAAC CCCAGAATAT GGGGAAATGC CCCCGATGTA GTCTAG        46

(2) INFORMATION FOR SEQ ID NO:56:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:56:

AGCCGGTAAC CCCAGAATAT GGGGAAATGT GCCCGATGTA GTCTAG        46

(2) INFORMATION FOR SEQ ID NO:57:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:57:

AGCCGGTAAC CCCAGAATAT GGGGAAATGA TCCCGATGTA GTCTAG        46

(2) INFORMATION FOR SEQ ID NO:58:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:58:

AGCCGGTAAC CCCAGAATAT GGGGAAATCA GCCCGATGTA GTCTAG        46

(2) INFORMATION FOR SEQ ID NO:59:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:59:

AGCCGGTAAC CCCAGAATAT GGGGAAATTT TCCCGATGTA GTCTAG        46

(2) INFORMATION FOR SEQ ID NO:60:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:60:

AGCCGGTAAC CCCAGAATAT GGGGAAATCA TCCCGATGTA GTCTAG        46

(2) INFORMATION FOR SEQ ID NO:61:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:61:

AGCCGGTAAC CCCAGAATAT GGGGAAATGA ACCCGATGTA GTCTAG                46

(2) INFORMATION FOR SEQ ID NO:62:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:62:

AGCCGGTAAC CCCAGAATAT GGGGAAATCG GCCCGATGTA GTCTAG                46

(2) INFORMATION FOR SEQ ID NO:63:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:63:

AGCCGGTAAC CCCAGAATAT GGGGAAATGG ACCCGATGTA GTCTAG                46

(2) INFORMATION FOR SEQ ID NO:64:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:64:

AGCCGGTAAC CCCAGAATAT GGGGAAATGG TCCCGATGTA GTCTAG                46

(2) INFORMATION FOR SEQ ID NO:65:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:65:

AGCCGGTAAC CCCAGAATAT GGGGAAATCC ACCCGATGTA GTCTAG                46

(2) INFORMATION FOR SEQ ID NO:66:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:66:

AGCCGGTAAC CCCAGAATAT GGGGAAATAA CCCCGATGTA GTCTAG                46

(2) INFORMATION FOR SEQ ID NO:67:

(i) SEQUENCE CHARACTERISTICS:

(A) LENGTH: 46 base pairs
            (B) TYPE: nucleic acid
            (C) STRANDEDNESS: single
            (D) TOPOLOGY: linear (xi) SEQUENCE DESCRIPTION: SEQ ID NO:67:

AGCCGGTAAC CCCAGAATAT GGGGATCATC ACCCGATGTA GTCTAG                46

(2) INFORMATION FOR SEQ ID NO:68:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:68:

GGATTATTGG GGTCATGGTG CTA                                         23

(2) INFORMATION FOR SEQ ID NO:69:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:69:

AGCACCATGA CCCCAATAAT CCATGGCTGC TTTGTTACC                        39

(2) INFORMATION FOR SEQ ID NO:70:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:70:

AGCACCATGA CCCCAATAAT CCATGGCACG TTTGTTACC                        39

(2) INFORMATION FOR SEQ ID NO:71:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:71:

AGCACCATGA CCCCAATAAT CCATGGCGTT TTTGTTACC                        39

(2) INFORMATION FOR SEQ ID NO:72:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:72:

AGCACCATGA CCCCAATAAT CCATGGCGTC TTTGTTACC                        39

(2) INFORMATION FOR SEQ ID NO:73:

(i) SEQUENCE CHARACTERISTICS:
            (A) LENGTH: 39 base pairs (B) TYPE: nucleic acid
        (C) STRANDEDNESS: single
        (D) TOPOLOGY: linear (xi) SEQUENCE DESCRIPTION: SEQ ID NO:73:

AGCACCATGA CCCCAATAAT CCATGGCGCA TTTGTTACC                       39

(2) INFORMATION FOR SEQ ID NO:74:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:74:

AGCACCATGA CCCCAATAAT CCATGGCTTC TTTGTTACC                       39

(2) INFORMATION FOR SEQ ID NO:75:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:75:

AGCACCATGA CCCCAATAAT CCATGGCCTG TTTGTTACC                       39

(2) INFORMATION FOR SEQ ID NO:76:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:76:

AGCACCATGA CCCCAATAAT CCATGGCGCC TTTGTTACC                       39

(2) INFORMATION FOR SEQ ID NO:77:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:77:

AGCACCATGA CCCCAATAAT CCATGGCGTG TTTGTTACC                       39

(2) INFORMATION FOR SEQ ID NO:78:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:78:

AGCACCATGA CCCCAATAAT CCATGGCGAT TTTGTTACC                       39

(2) INFORMATION FOR SEQ ID NO:79:

(i) SEQUENCE CHARACTERISTICS:
        (A) LENGTH: 39 base pairs
        (B) TYPE: nucleic acid (C) STRANDEDNESS: single
        (D) TOPOLOGY: linear (xi) SEQUENCE DESCRIPTION: SEQ ID NO:79:

AGCACCATGA CCCCAATAAT CCATGGCCAG TTTGTTACC        39

(2) INFORMATION FOR SEQ ID NO:80:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:80:

AGCACCATGA CCCCAATAAT CCATGGCTTT TTTGTTACC        39

(2) INFORMATION FOR SEQ ID NO:81:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:81:

AGCACCATGA CCCCAATAAT CCATGGCCAT TTTGTTACC        39

(2) INFORMATION FOR SEQ ID NO:82:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:82:

AGCACCATGA CCCCAATAAT CCATGGCGAA TTTGTTACC        39

(2) INFORMATION FOR SEQ ID NO:83:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:83:

AGCACCATGA CCCCAATAAT CCATGGCCGG TTTGTTACC        39

(2) INFORMATION FOR SEQ ID NO:84:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:84:

AGCACCATGA CCCCAATAAT CCATGGCGGA TTTGTTACC        39

(2) INFORMATION FOR SEQ ID NO:85:

(i) SEQUENCE CHARACTERISTICS:
        (A) LENGTH: 39 base pairs
        (B) TYPE: nucleic acid
        (C) STRANDEDNESS: single (D) TOPOLOGY: linear (xi) SEQUENCE DESCRIPTION: SEQ ID NO:85:

AGCACCATGA CCCCAATAAT CCATGGCGGT TTTGTTACC                    39

(2) INFORMATION FOR SEQ ID NO:86:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (xi) SEQUENCE DESCRIPTION: SEQ ID NO:86:

AGCACCATGA CCCCAATAAT CCATGGCCCA TTTGTTACC                    39

(2) INFORMATION FOR SEQ ID NO:87:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (xi) SEQUENCE DESCRIPTION: SEQ ID NO:87:

AGCACCATGA CCCCAATAAT CCATGGCGTA TTTGTTACC                    39

(2) INFORMATION FOR SEQ ID NO:88:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (xi) SEQUENCE DESCRIPTION: SEQ ID NO:88:

AGCACCATGA CCCCAATAAT CCATGGCAAC TTTGTTACC                    39

(2) INFORMATION FOR SEQ ID NO:89:

(i) SEQUENCE CHARACTERISTICS:
                (A) LENGTH: 39 base pairs
                (B) TYPE: nucleic acid
                (C) STRANDEDNESS: single
                (D) TOPOLOGY: linear (xi) SEQUENCE DESCRIPTION: SEQ ID NO:89:

AGCACCATGA CCCCAATAAT CCATTCATCA TTTGTTACC                    39

(2) INFORMATION FOR SEQ ID NO:90:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO:90:

GCGTAGTTTG GCTACAGT                                           18

(2) INFORMATION FOR SEQ ID NO:91:

(i) SEQUENCE CHARACTERISTICS:
                (A) LENGTH: 31 base pairs
                (B) TYPE: nucleic acid
                (C) STRANDEDNESS: single
                (D) TOPOLOGY: linear (xi) SEQUENCE DESCRIPTION: SEQ ID NO:91:

AGCCAAACTA CGCATGTTCC ACCCACGTTC G                              31

(2) INFORMATION FOR SEQ ID NO:92:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:92:

AGCCAAACTA CGCATGCACC ACCCACGTTC G                              31

(2) INFORMATION FOR SEQ ID NO:93:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:93:

AGCCAAACTA CGCATCGTCC ACCCACGTTC G                              31

(2) INFORMATION FOR SEQ ID NO:94:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:94:

AGCCAAACTA CGCATAACCC ACCCACGTTC G                              31

(2) INFORMATION FOR SEQ ID NO:95:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:95:

AGCCAAACTA CGCATGACCC ACCCACGTTC G                              31

(2) INFORMATION FOR SEQ ID NO:96:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:96:

AGCCAAACTA CGCATTGCCC ACCCACGTTC G                              31

(2) INFORMATION FOR SEQ ID NO:97:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:97:

AGCCAAACTA CGCATGAACC ACCCACGTTC G                                                  31

(2) INFORMATION FOR SEQ ID NO:98:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:98:

AGCCAAACTA CGCATCAGCC ACCCACGTTC G                                                  31

(2) INFORMATION FOR SEQ ID NO:99:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:99:

AGCCAAACTA CGCATGGCCC ACCCACGTTC G                                                  31

(2) INFORMATION FOR SEQ ID NO:100:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:100:

AGCCAAACTA CGCATCACCC ACCCACGTTC G                                                  31

(2) INFORMATION FOR SEQ ID NO:101:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:101:

AGCCAAACTA CGCATATCCC ACCCACGTTC G                                                  31

(2) INFORMATION FOR SEQ ID NO:102:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:102:

AGCCAAACTA CGCATCTGCC ACCCACGTTC G                                                  31

(2) INFORMATION FOR SEQ ID NO:103:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:103:

AGCCAAACTA CGCATAAACC ACCCACGTTC G					31

(2) INFORMATION FOR SEQ ID NO:104:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:104:

AGCCAAACTA CGCATATGCC ACCCACGTTC G					31

(2) INFORMATION FOR SEQ ID NO:105:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:105:

AGCCAAACTA CGCATTTCCC ACCCACGTTC G					31

(2) INFORMATION FOR SEQ ID NO:106:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:106:

AGCCAAACTA CGCATCCGCC ACCCACGTTC G					31

(2) INFORMATION FOR SEQ ID NO:107:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:107:

AGCCAAACTA CGCATTCCCC ACCCACGTTC G					31

(2) INFORMATION FOR SEQ ID NO:108:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:108:

AGCCAAACTA CGCATACCCC ACCCACGTTC G					31

(2) INFORMATION FOR SEQ ID NO:109:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:109:

AGCCAAACTA CGCATTGGCC ACCCACGTTC G                31

(2) INFORMATION FOR SEQ ID NO:110:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:110:

AGCCAAACTA CGCATTGACC ATGAACGTTC G                31

(2) INFORMATION FOR SEQ ID NO:111:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:111:

AGCCAAACTA CGCATGTTCC AGCAACGTTC G                31

(2) INFORMATION FOR SEQ ID NO:112:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:112:

AGCCAAACTA CGCATGTTCC ACGTACGTTC G                31

(2) INFORMATION FOR SEQ ID NO:113:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:113:

AGCCAAACTA CGCATGTTCC AAACACGTTC G                31

(2) INFORMATION FOR SEQ ID NO:114:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:114:

AGCCAAACTA CGCATGTTCC AGACACGTTC G                31

(2) INFORMATION FOR SEQ ID NO:115:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:115:

AGCCAAACTA CGCATGTTCC ATGCACGTTC G                31

(2) INFORMATION FOR SEQ ID NO:116:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:116:

AGCCAAACTA CGCATGTTCC AGAAACGTTC G                                                  31

(2) INFORMATION FOR SEQ ID NO:117:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:117:

AGCCAAACTA CGCATGTTCC ACAGACGTTC G                                                  31

(2) INFORMATION FOR SEQ ID NO:118:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:118:

AGCCAAACTA CGCATGTTCC AGGCACGTTC G                                                  31

(2) INFORMATION FOR SEQ ID NO:119:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:119:

AGCCAAACTA CGCATGTTCC ACACCGTTCG                                                    30

(2) INFORMATION FOR SEQ ID NO:120:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:120:

AGCCAAACTA CGCATGTTCC AATCACGTTC G                                                  31

(2) INFORMATION FOR SEQ ID NO:121:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:121:

AGCCAAACTA CGCATGTTCC ACTGACGTTC G                                                  31

(2) INFORMATION FOR SEQ ID NO:122:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:122:

AGCCAAACTA CGCATGTTCC AAAAACGTTC G                                    31

(2) INFORMATION FOR SEQ ID NO:123:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:123:

AGCCAAACTA CGCATGTTCC AATGACGTTC G                                    31

(2) INFORMATION FOR SEQ ID NO:124:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:124:

AGCCAAACTA CGCATGTTCC ATTCACGTTC G                                    31

(2) INFORMATION FOR SEQ ID NO:125:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:125:

AGCCAAACTA CGCATGTTCC ATCCACGTTC G                                    31

(2) INFORMATION FOR SEQ ID NO:126:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:126:

AGCCAAACTA CGCATGTTCC AACCACGTTC G                                    31

(2) INFORMATION FOR SEQ ID NO:127:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:127:

AGCCAAACTA CGCATGTTCC ATGGACGTTC G                                    31

(2) INFORMATION FOR SEQ ID NO:128:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:128:

AGCCAAACTA CGCATGTTCC ATACACGTTC G                                            31

(2) INFORMATION FOR SEQ ID NO:129:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:129:

AGCCAAACTA CGCATGTTCC AGTTACGTTC G                                            31

(2) INFORMATION FOR SEQ ID NO:130:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:130:

CGATGCGTCC GGCGTAGA                                                          18

(2) INFORMATION FOR SEQ ID NO:131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:131:

GCTAGTTATT GCTCAGCGG                                                       19

(2) INFORMATION FOR SEQ ID NO:132:

(i) SEQUENCE CHARACTERISTICS:
        (A) LENGTH: 269 amino acids
        (B) TYPE: amino acid
        (C) STRANDEDNESS:
        (D) TOPOLOGY: linear (xi) SEQUENCE DESCRIPTION: SEQ ID NO:132:

```
Met Glu Val Gln Leu Gln Gln Ser Gly Pro Glu Leu Val Lys Pro Gly
 1               5                  10                  15

Ala Ser Val Arg Met Ser Cys Lys Ser Ser Gly Tyr Ile Phe Thr Asp
                20                  25                  30

Phe Tyr Met Asn Trp Val Arg Gln Ser His Gly Lys Ser Leu Asp Tyr
            35                  40                  45

Ile Gly Tyr Ile Ser Pro Tyr Ser Gly Val Thr Gly Tyr Asn Gln Lys
        50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95
```

```
Cys Ala Gly Ser Ser Gly Asn Lys Trp Ala Met Asp Tyr Trp Gly His
            100             105             110
Gly Ala Ser Val Thr Val Ser Ser Gly Gly Gly Ser Gly Gly Gly
            115             120             125
Gly Ser Gly Gly Gly Ser Asp Ile Val Leu Thr Gln Thr Pro Pro
    130             135             140
Ser Leu Pro Val Ser Leu Gly Asp Gln Ala Thr Ile Ser Cys Arg Ser
145             150             155             160
Ser Gln Ser Leu Val His Ser Asn Gly Asn Thr Tyr Leu Asn Trp Tyr
            165             170             175
Leu Gln Lys Ala Gly Gln Ser Pro Lys Leu Leu Ile Tyr Lys Val Ser
            180             185             190
Asn Arg Phe Ser Gly Val Pro Ala Arg Phe Ser Gly Ser Gly Ser Gly
        195             200             205
Ser Asp Phe Thr Leu Thr Ile Asp Arg Val Glu Glu Asp Asp Ala Ala
    210             215             220
Ile Tyr Tyr Cys Ser Gln Thr Thr His Val Pro Pro Thr Phe Gly Ser
225             230             235             240
Gly Thr Lys Leu Glu Ile Ile Arg Ala Ser Gln Pro Glu Leu Ala Pro
            245             250             255
Glu Asp Pro Glu Asp Val Glu His His His His His
            260             265
```

IN VITRO SCANNING SATURATION MUTAGENESIS OF PROTEINS

The present application is a continuation-in-part of co-pending U.S. Provisional Patent Application Serial No. 60/045,409 filed May 1, 1997. The entire text of the above-referenced disclosure is specifically incorporated by reference herein without disclaimer.

BACKGROUND OF THE INVENTION

A. Field of the Invention

The invention relates generally to the field of protein chemistry. More specifically, the invention relates to methods employed in the rapid generation of a large number of protein mutants. In one embodiment, mutant proteins are developed using PCR mutagenesis in combination with in vitro transcription/translation.

B. Related Art

Understanding the chemical basis of protein structure and function is one of the most important goals in biology. Studies over the last decade have attempted to determine how protein structure dictates biological function. Site-specific mutagenesis has been a powerful tool in these studies. Structure-guided, site-specific mutagenesis represents a powerful tool for the dissection and engineering of protein-ligand interactions (Wells, 1996; Braisted and Wells, 1996). Typically, residues suspected of contacting the ligand are subjected to a limited set of substitutions with other amino acids and their effects on binding are determined. Several studies, in particular with the T4 lysozyme (Matthews, 1995) and the human growth hormone (hGH)-hGH receptor complex (Wells and deVos, 1993), have combined information derived from crystal structures of a protein with site-specific mutagenesis to analyze the role of contact residues with the ligand. Recently, the role of all the contact residues in the hGH receptor protein was analyzed by replacement with alanines to investigate the effects of side chain interactions without creating large-scale perturbations in protein conformation. (Clackson and Wells, 1995; Cunningham et al., 1989). The results clearly show that out of the thirty-three amino acids in the hGH receptor that are in van der Waals contact with the high affinity binding site of human growth hormone, two amino acids are responsible for over 75% of the binding energy. This result, which could not have been predicted on the basis of the crystal structure of the complex alone, demonstrated that a very small subset of the residues at a protein-ligand interface can be responsible for the majority of binding energy. This study demonstrates the value of mutagenesis at a large number of residues within a protein. However, the study of hGH was limited to the substitution of alanine at a relatively small number of amino acids within the protein, and the substitution of functional residues with alanine, or any other single amino acid, can give misleading results regarding their mechanistic importance (Warren et al., 1996).

In addition to site-specific mutagenesis, libraries generated by random mutagenesis have been employed to reveal principles of protein structure. For example, cassette mutagenesis has been used to probe the "information content" of polypeptide sequences (Reidhaar-Olson and Sauer, 1989; Davidson and Sauer, 1994; Davidson et al., 1995). These studies involve the construction of polypeptide mutants composed of random combinations of selected amino acids. The mutants are then analyzed for their thermal denaturation properties. This study, utilizing existing technology to generate and characterize a relatively large number of mutant proteins, was very labor- and time-intensive.

Thus, the comprehensive understanding of protein function typically involves the construction of hundreds, and possibly thousands of mutants. The logistics of such large scale mutagenesis experiments can be prohibitive. For each mutant protein, using current methodology, the appropriate gene construct must be made, a host organism must be transformed with the DNA, transformants must be selected and screened for expression of the protein, and finally, the host cells must be grown to produce the protein. Using currently available methods, the production of a single mutant polypeptide typically takes a minimum of two weeks of work by experienced personnel. While current methods for site specific mutagenesis may be acceptable in structure-guided studies where only a few amino acid substitutions may be of interest, it is impractical and prohibitively expensive when a hundred or more mutants need to be generated and analyzed.

As a target for mutagenesis studies, attention continues to be focused on antibodies, largely because they define a paradigm of high affinity protein binding and are among the most important classes of commercial protein molecules. Antibodies are nearly ideal reagents for the detection of analytes that are present in minute quantities in highly complex samples, for example soil samples or biological fluids. However, because of inherent limitation of the immune system and of hybridoma technology there are many cases in which it has not been possible to produce monoclonal antibodies with the requisite affinity or specificity for a particular application. Fortunately, recent advances in protein design and characterization techniques have paved the way for the engineering of antibodies with desired functions.

At present, the engineering of antibodies that recognize and bind to antigens with higher affinity, are covalently linked to effector molecules such as toxins, exhibit catalytic activity, or have been modified for better in vivo availability and stability represents an exciting and rapidly evolving field (Morrison, 1992; Lillehoj and Malik 1993). Antibodies with tailored properties hold great promise as pharmaceutical reagents, for bioseparations and, perhaps most importantly, as diagnostic reagents in immunoassays.

Antigen binding is determined primarily, but not exclusively, by amino acid residues in the antibody hypervariable or complementarity determining regions (CDRs) I, II, and III of the heavy (H) and light (L) chains. There is evidence that the antigen binding site exhibits a fair degree of plasticity in that a number of amino acid substitutions are tolerated and occasionally improve affinity (Chen et al., 1995; Short et al., 1995). Studies have also demonstrated that the second shell, as well as contact residues, can play an important role in stabilizing the overall conformation of an antibody binding pocket and in turn affect the affinity and fine specificity of the antibody (Schildbach et al., 1993a, Schildbach et al., 1993b, Schildbach et al., 1994).

One method used for the screening of antibody libraries is phage display (Short et al., 1995). In combination with mutagenesis techniques, phage display has been used to explore the effect of amino acid substitutions on antigen affinity. Such large scale studies can provide important information concerning issues such as: (i) the identity of residues that determine antigen affinity and specificity; (ii) what molecular interactions dominate the energetics of binding; (iii) the molecular basis of affinity maturation (Chen et al., 1995; Brown et al., 1996); and (iv) engineering of antibodies tailored for specific applications in biotechnology (Harrison et al., 1996; Burton and Barbas, 1994).

However, while phage display technology can succeed in the identification of sequence motifs that result in a high affinity towards a desired antigen, this approach complements, and does not substitute for, site-specific mutagenesis. First, since only the amino acid(s) that are compatible with high affinity binding can be identified in a biopanning experiment, it is not possible to examine the effect of other amino acid substitutions that may result in slightly lower affinity, such as second shell residues. Second, the polypeptide sequences that can be isolated using phage display are limited by biological constraints. If a particular amino acid is incompatible with the biogenesis or the propagation of the bacteriophage particle then, the corresponding clone cannot be isolated. And third, the isolation of antibody mutants exhibiting alterations in fine specificity or small changes in affinity is technically difficult. These limitations are particularly important for saturation mutagenesis experiments where specific residues are replaced with all nineteen amino acids.

In recent years, there has been increased interest in the use of in vitro protein synthesis to produce polypeptides for biochemical studies. Methods for in vitro translation to were used to generate C-terminal deletions in the β subunit of tryptophan synthase which were then employed to localize the epitope sequences of a panel of monoclonal antibodies (Friquet et al., 1993). Mutants of the proliferating cell nuclear antigen (PCNA) have also been synthesized using an in vitro to probe for sequences important for the oligomerization of the protein (Brand et al. 1994). In another application, a rabbit reticulocyte in vitro transcription/translation system was used to identify antibody cDNAs that were derived from transcripts with the correct VJ recombination and thus could give rise to the full length molecule (Nicholls et al., 1993).

Thus far, in vitro protein synthesis has not been employed extensively for protein engineering studies. The main reason is that the amount of polypeptide obtained from in vitro transcription/translation reactions generally is not adequate for rigorous biophysical analysis. However, the protein yield obtained by in vitro synthesis is more than adequate for determination of function, such as ligand binding or catalysis. Protein yield also generally is adequate for general studies such as folding properties and expression levels.

It is well appreciated that comprehensive information on the functional significance and information content of a given residue of proteins in general, and antibodies in particular, can best be obtained by saturation mutagenesis in which all 19 amino acid substitutions are examined. A method which would allow for the facile site-saturation of a given protein, as well as being amenable to screening methods, would provide a significant advance in the discovery process for protein-ligand interactions in general, and antibody-antigen interactions in particular.

At present, while tools are available through which multi-residue saturation mutagenesis can be performed, the current methodology is impractical for the generation of a large number of mutants (Hilton et al., 1996). For each mutant protein, the appropriate gene construct must be made, the DNA must be transformed into a host organism, transformants need to be selected and screened for expression of the protein, the cells must be grown to produce the protein, and finally the recombinant mutant protein must be isolated. There have been only a handful of studies where one, or at most a few residues in an antibody have been subjected to saturation mutagenesis. Even in those studies, only some of the mutants were examined in detail (Ito et al., 1993; Chen et al., 1995; Brummel et al., 1993). Clearly, there remains a need for development of a system to allow hundreds, and possibly even thousands, of site specific protein mutants to be studied in a systematic fashion. In particular, there also remains a need for the development of a system for the generation and analysis of a large number of antibody mutants.

SUMMARY OF THE INVENTION

It is, therefore, a goal of the present invention to provide compositions and methods relating to the generation and characterization of large numbers of protein mutants for the purpose of selecting new proteins with novel and/or improved characteristics. Methods are provided for in vitro scanning saturation mutagenesis. The method of the present invention combines the generation of a DNA template, incorporating a large number of mutations, at predetermined sites, by chemical or enzymatic processes, and the subsequent generation of a new protein from the mutagenized DNA template using in vitro transcription/translation.

The present invention provides a method of selecting a polypeptide variant having analyte binding activity comprising the steps of providing a DNA segment encoding a polypeptide, or analyte-binding fragment thereof; generating a set of variant DNA segments, wherein the DNA segments encode substitution variants at single residue of the polypeptide or analyte-binding fragment thereof; expressing each of the substitution variants using in vitro transcription/translation; selecting the polypeptide variant based on analyte binding activity. In certain embodiments, the variant DNA segments further contain other substitution, deletion or insertion mutations not involving the single residue. In particular embodiments the gene encodes an antibody. The set of variants DNA segments encodes each of nineteen possible amino acid substitutions at the single residue of the polypeptide or fragment. In a preferred aspect of the present invention the analyte binding activity is assessed by ELISA.

In particular embodiments, the generating comprises a enzymatically synthesized, site-direct mutagenesis. In preferred embodiments, the enzymatic synthesis comprises PCR. In particular aspects the transcription/translation step may employ a prokaryotic expression system. In other aspects, the gene is under the transcriptional control of a bacterial promoter. In preferred embodiments, the promoter may be T7, trc, tac, lpp-lac, trp, tet, lac, PBAD, phoA or PL or any promoter described in Table 1.

The present invention further provides a method of identifying an antibody variant comprising the steps of providing a DNA segment encoding a antibody, or antigen-binding fragment thereof; providing a set of primers that encode all nineteen amino acid variants at a single residue of the antibody or antigen-binding fragment thereof; performing PCR reactions on the DNA segment, using the set of primers, to generate a set of variant DNA segments encoding nineteen amino acid substitution variants at the single residue of the antibody or antigen binding fragments thereof; expressing each of the substitution variants using in vitro transcription/translation; identifying the antibody variant by antigen binding activity. In one aspect, the primers are between about 10 and about 50 bases in length. In another aspect, the DNA segment encodes a single-chain antibody. In other embodiments, the antibody may be a catalytic antibody, and the antibody variant further is identified by means of enzymatic activity. In certain other aspects it is contemplated that the antibody variant or antigen binding fragment thereof has a binding affinity for the antigen greater than the antibody. In yet further aspects it is contemplated that the antibody variant or antigen-binding fragment thereof exhibits a lesser degree of cross-reactivity with related antigen species than does the antibody.

The present invention contemplates an antibody identified according to a method comprising the steps of providing a DNA segment encoding a antibody, or antigen-binding fragment thereof; providing a set of primers that encode all nineteen amino acid variants at a single residue of the antibody or antigen-binding fragment thereof, performing PCR reactions on the DNA segment, using the set of primers, to generate a set of variant DNA segments encoding nineteen amino acid substitution variants at the single residue of the antibody or antigen binding fragments thereof, expressing each of the substitution variants using in vitro transcription/translation; identifying an antibody by antigen binding activity.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Points of difference compared to digoxin are indicated with the arrows.

Figure 2A:
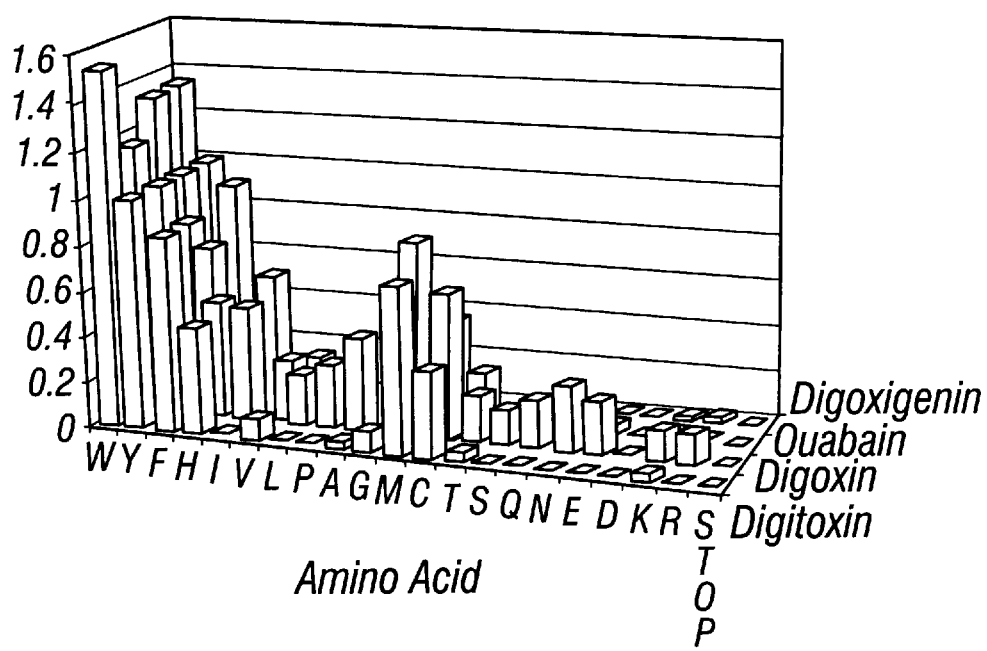
Figure 2B:
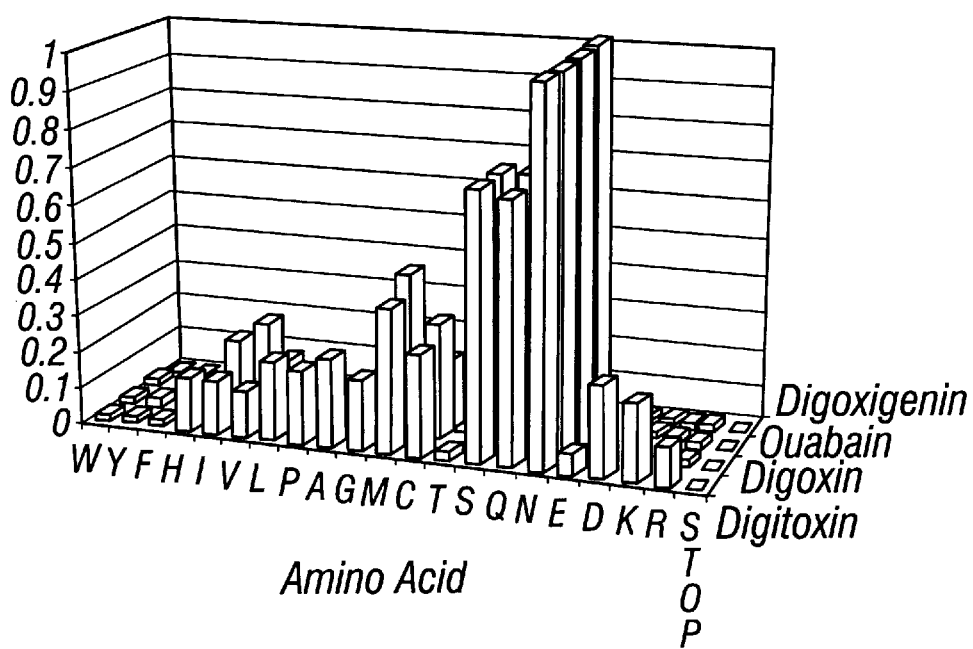
Figure 2C:
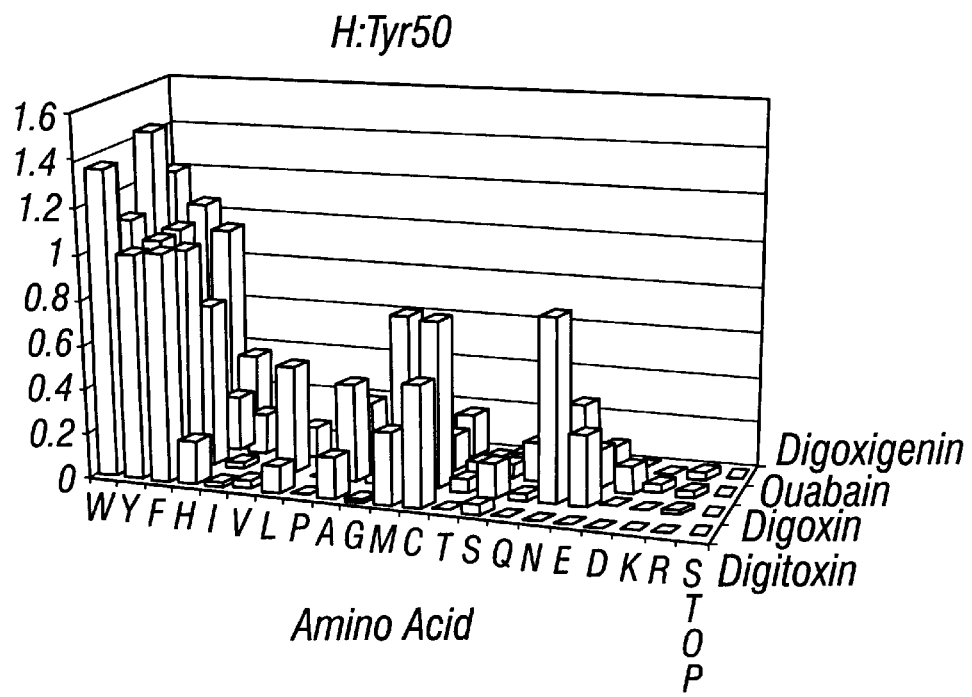
Figure 2D:
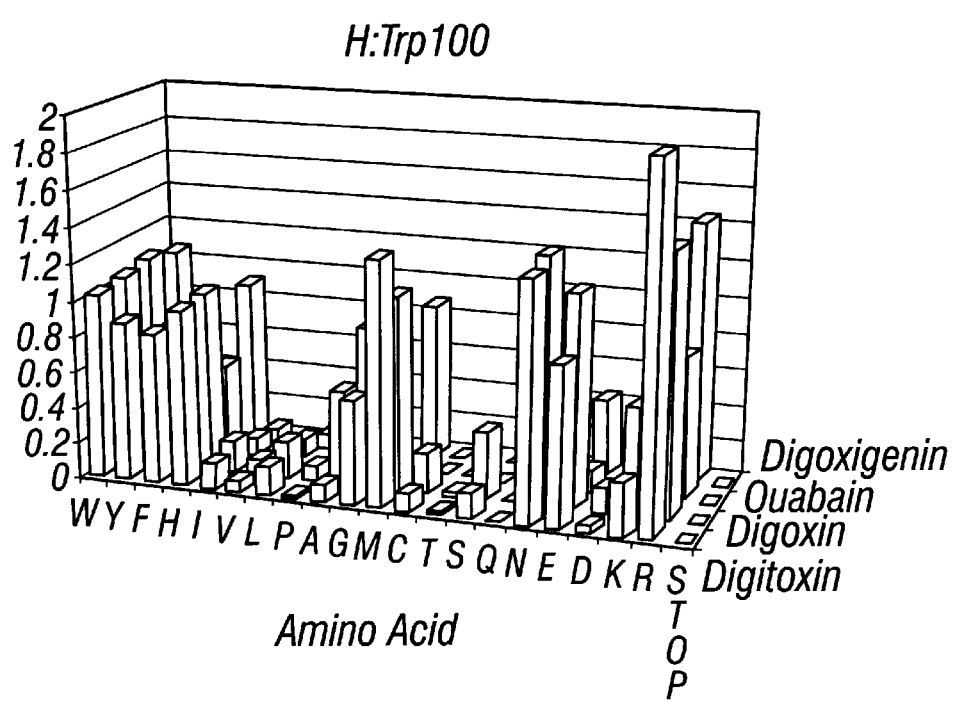
Figure 2E:
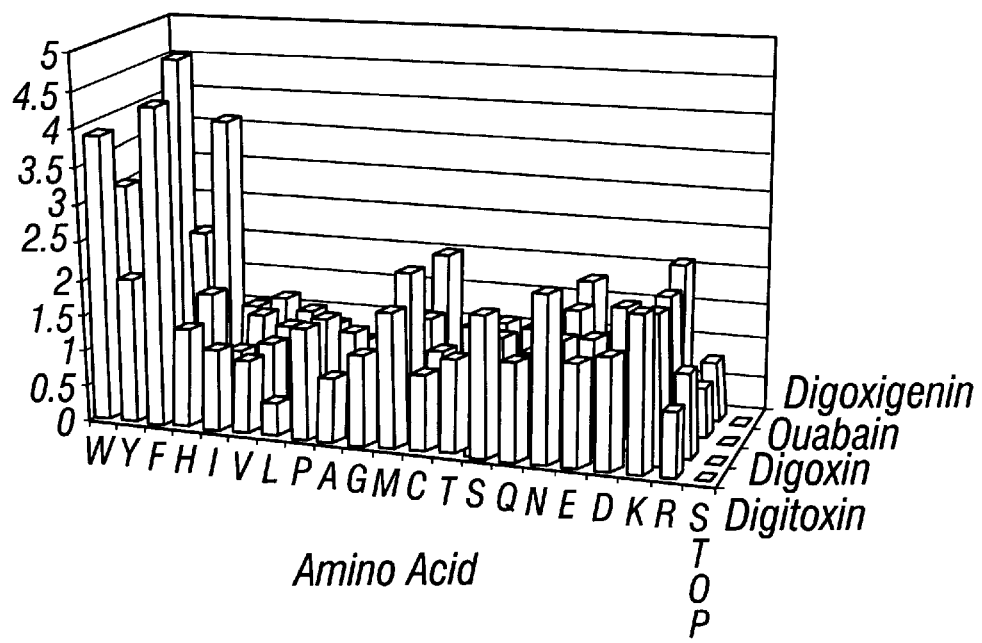
Figure 2F:
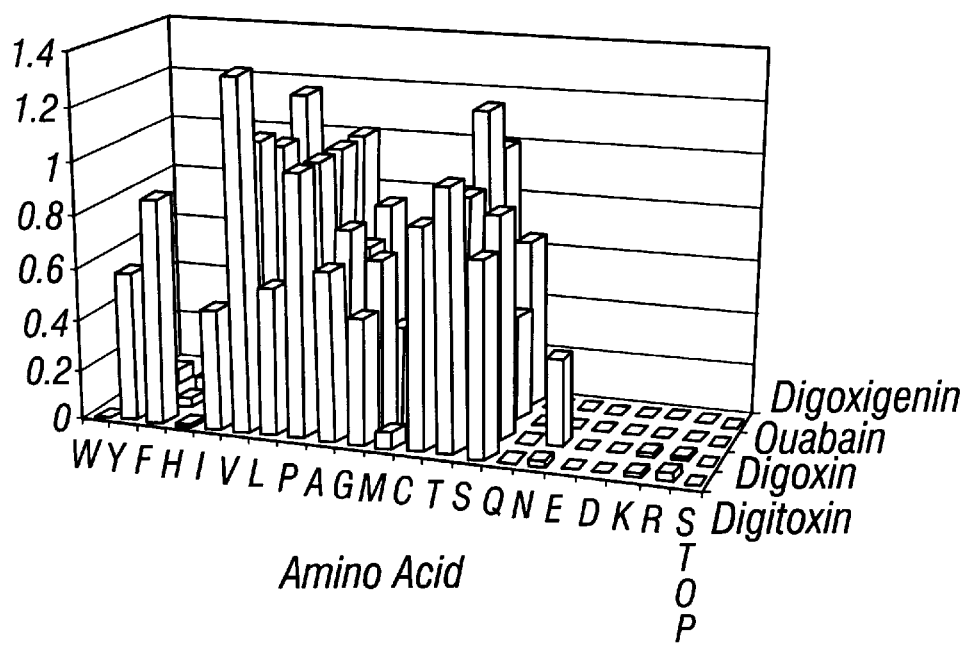
Figure 2G:
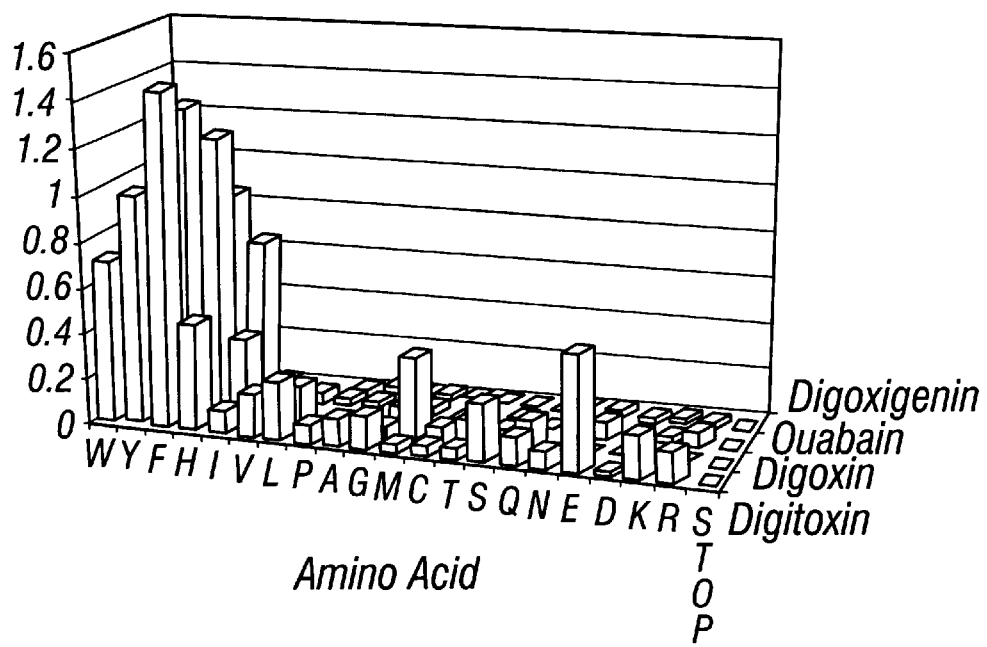
Figure 2H:
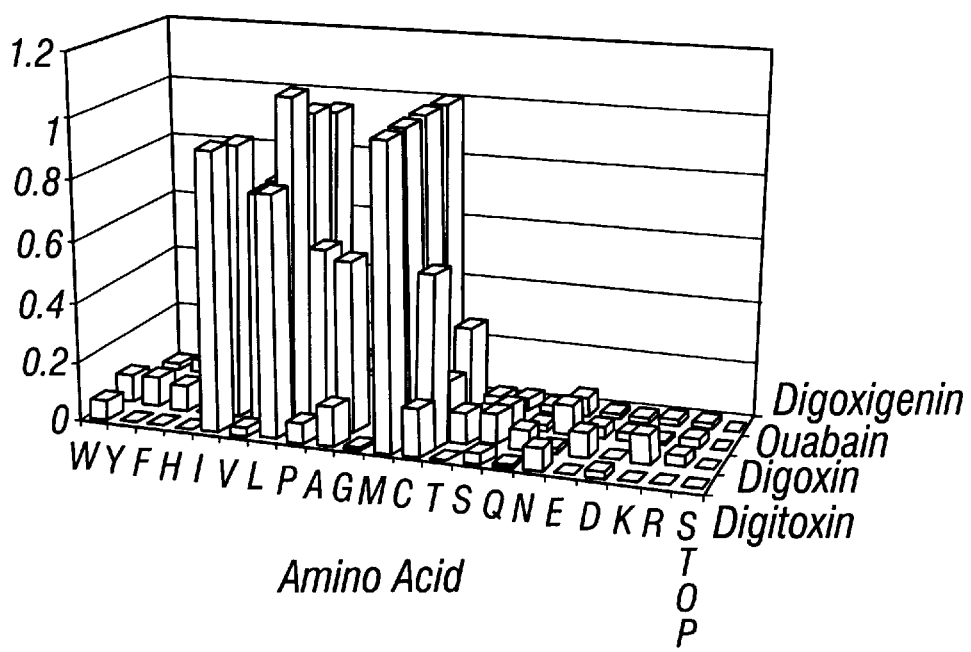
Figure 2I:
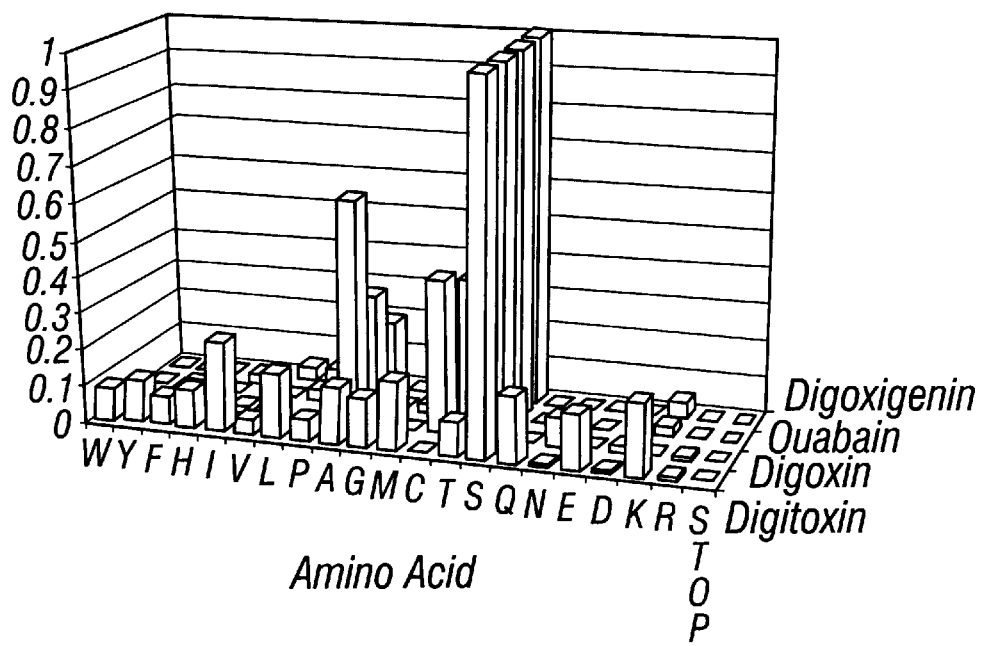
Figure 2J:
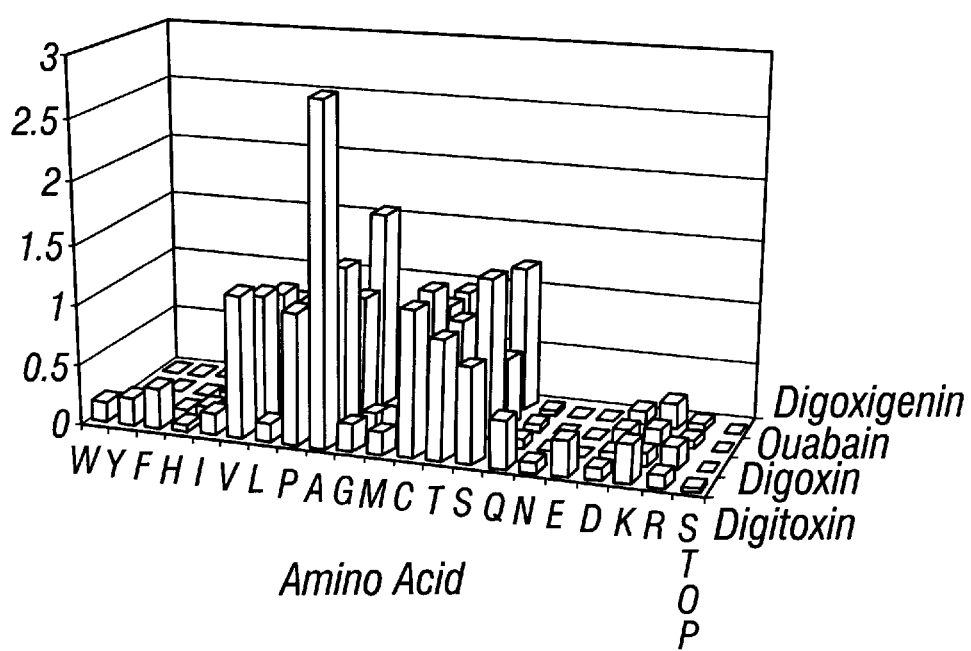

FIGS. 2A–J. Histograms of the ELISA data for the different mutant proteins binding to digoxin, digitoxin, digoxigenin, and ouabain. FIG. 2A: Mutations of residue H:Tyr33. FIG. 2B: Mutations of residue H:Asn35. FIG. 2C: Mutations of residue H:Tyr50. FIG. 2D: Mutations of residue H:Trp100. FIG. 2E: Mutations of residue L:Val94. FIG. 2F: Mutations of residue L:Pro96. FIG. 2G: Mutations of residue H:Tyr47. FIG. 2H: Mutations of residue H:Met100B. FIG. 2I: Mutations of residue H:Ser95. FIG. 2J: Mutations of residue L:Thr91. The plotted values correspond to the absorbance observed in ELISA measured at 405 nm on a microplate autoreader when the ABTS reaction was still in the linear range, a fact that was confirmed by taking several time points per plate. For each cardiac glycoside being investigated (digoxin, digitoxin, digoxigenin, ouabain) the absorbances for each mutant were linearly scaled to that of the wild-type scFv(Dig), which was assigned a value of 1.0, then plotted in the histograms. Wild-type scFv(Dig) was included on every ELISA plate to provide an internal calibration of the data.

Figure 3A:
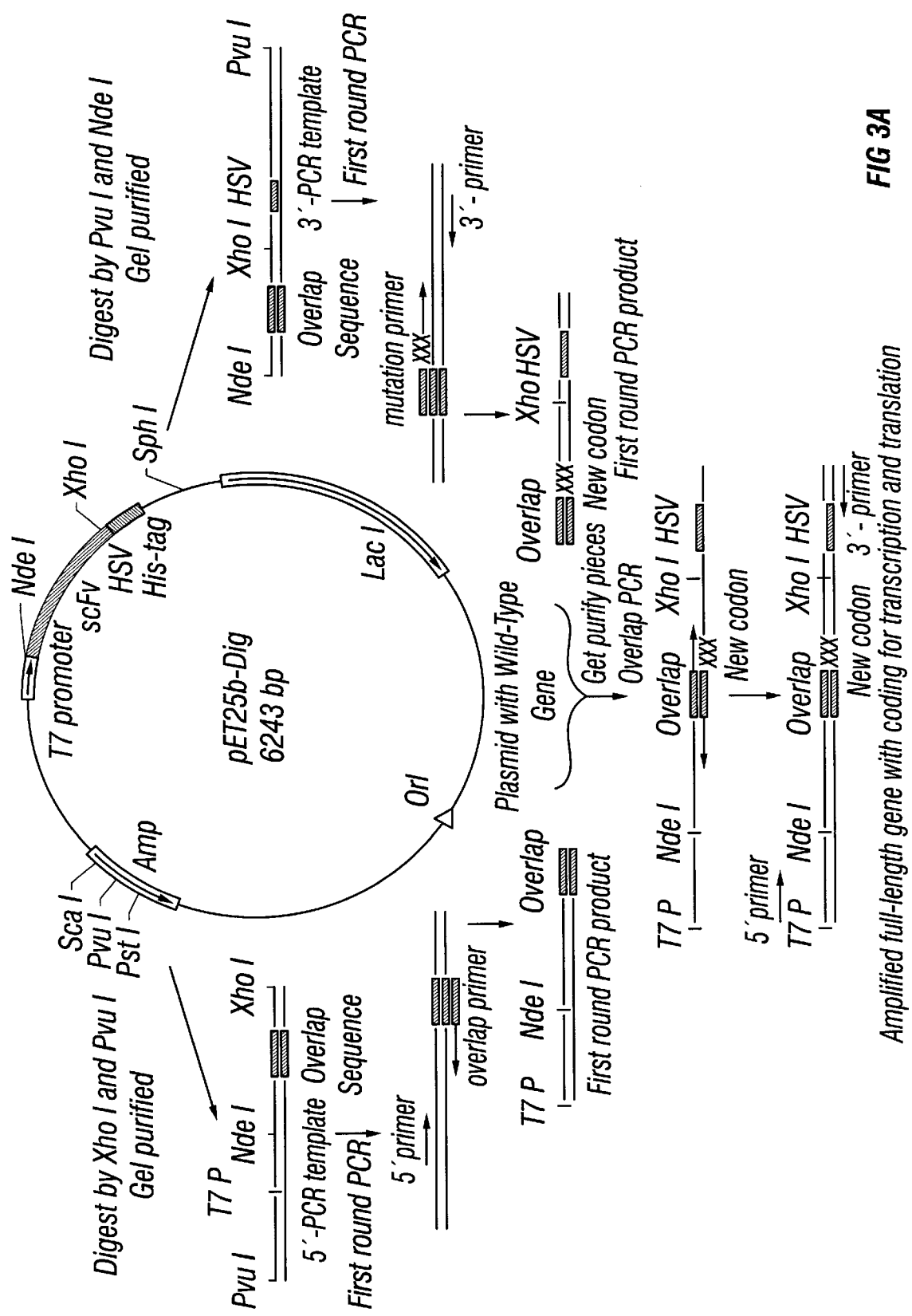
Figure 3B:
Figure 3B:
Figure 3B:
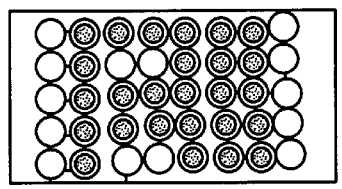
Figure 3B:
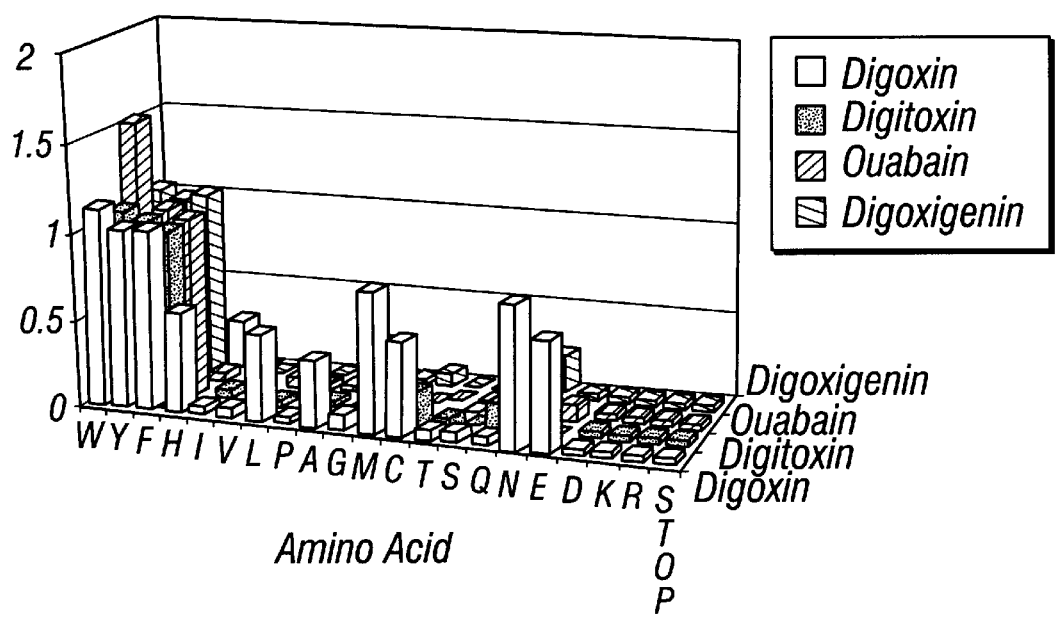

FIG. 3A and FIG. 3B. FIG. 3A Scheme for the overlap PCR production of mutant constructs t be used as templates for in vitro transcription-translation reactions. FIG. 3B Scheme showing how the gene constructs are used to make mutant scFV(Dig) through in vitro transcription/translation followed by ELISA analysis.

DETAILED DESCRIPTION OF THE PREFERRED EMBODIMENTS

As stated above, there is a great need for improved methods that permit the rapid, efficient generation and screening of variant polypeptides. The present invention addresses this need by providing, in one aspect, methods for the generation of a large number of mutations within a protein, and the subsequent rapid assaying of mutants for appropriate characteristics. The principal underlying this technology is that by integrating DNA mutagenesis techniques and in vitro transcription/translation, it is possible to generate and analyze large numbers of mutant proteins, resulting in about a ten-fold reduction in time over currently available techniques. The use of in vitro techniques for transcription/translation of mutant polypeptides eliminates the need for many of the high cost, labor intensive cloning procedures currently used to express mutant proteins.

In the present invention, the mutagenized DNA products are used directly as the template for in vitro synthesis of the corresponding mutant proteins. Because of the high efficiency with which all 19 amino acid substitutions can be generated at a single residue, it is possible to perform saturation mutagenesis on numerous residues of interest, either independently or in combination with other mutations within the protein. As used herein, "complete saturation" mutagenesis is defined as replacing a given amino acid within a protein, with the other 19 naturally-occurring amino acids.

A. The Present Invention

Using the appropriate oligonucleotide primers, PCR is used for the rapid synthesis of the DNA template containing one or more mutations in the binding protein gene. The protein gene is placed downstream of a T7 RNA polymerase promoter. Addition of T7 RNA polymerase and nucleosides results in synthesis of mRNA which is then translated in vitro by *E. coli* ribosomal (S30) extract, all in the same reaction. Of course, the T7 promoter and T7 RNA polymerase are only exemplary promoter/polymerase system, other promoters include, but are not limited, to those described in Table 1. For a comprehensive review of bacterial gene expression and bacterial promoters the skilled artisan is referred to Makrides (1996). Finally, aliquots from the translation mix are directly assayed for function by quantitative ELISA. The whole process of in vitro protein synthesis and antigen binding assay by ELISA consists of a series of mixing, incubation and washing steps. All of these steps are readily amenable to automation using laboratory robotic stations. An example of a binding protein is an antibody. The present invention exemplifies in vitro scanning mutagenesis using single chain antibodies (scFv) against cardiac glycosides, however, it is understood that any polypeptide that is able to bind to an analyte will be amenable to the present invention.

TABLE 1

Promoters used for high level gene expression in *E. coli*.

| Promoter (source) | Regulation | Induction |
|---|---|---|
| lac (*E. coli*) | lacI, lacI$^q$ | IPTG |
| | lacI(TS)$^a$, lacI$^q$(Ts)$^a$ | Thermal |
| | lacI(Ts)$^b$ | Thermal |
| trp (*E. coli*) | | Trp starvation, indole |
| | | acrylic acid |
| lpp (*E. coli*) | | IPTG, lactose$^c$ |
| phoA (*E. coli*) | phoB (positive), phoR (negative) | Phosphate starvation |
| recA (*E. coli*) | lex4 | Nalidixic acid |
| araBAD (*E. coli*) | araC | L-Arabinose |
| proU (*E. coli*) | | Osmolarity |
| cst-1 (*E. coli*) | | Glucose starvation |

TABLE 1-continued

Promoters used for high level gene expression in *E. coli*.

| Promoter (source) | Regulation | Induction |
|---|---|---|
| tetA (*E. coli*) | | Tetracycline |
| cad4 (*E. coli*) | cadR | pH |
| nar (*E. coli*) | fnr (FNR, NARL) | Anaerobic conditions, nitrate ion |
| tac, hybrid (*E. coli*) | lacI, lacI$^q$ lacI$^d$ | IPTG Thermal |
| trc, hybrid (*E. coli*) | lacI, lacI$^q$ lacI(Ts)$^a$, lacI$^q$(Ts)$^a$ | IPTG Thermal |
| lpp-lac, hybrid (*E. coli*) | lacI | IPTG |
| P$_{syn}$, synthetic (*E. coli*) | lacI, lacI$^q$ | IPTG |
| Starvation promoters (*E. coli*) | | |
| p$_L$ (λ) | λcIts857 | Thermal |
| p$_L$-9G-50, mutant (λ) | | Reduced temperature (<20° C.) |
| cspA (*E. coli*) | | Reduced temperature (<20° C.) |
| p$_R$, p$_L$, tandem (λ) | λcIts857 | Thermal |
| T7 (T7) | λcIts857 | Thermal |
| T7-lac operator (T7) | lacI$^q$ | IPTG |
| λp$_L$, p$_{T7}$, tandem (λ, T7) | λcIts857 | Thermal, IPTG |
| T3-lac operator (T3) | lacI$^q$ | IPTG |
| T5-lac operator (T5) | lacI$^q$, lacI | IPTG |
| T4 gene 32 (T4) | | T4 infection |
| nprM-lac operator (Bacillus spp.) | lacI$^q$ | IPTG |
| VHb (Vitreoscilla spp.) | | Oxygen, cAMP-CAP$^e$ |
| Protein A (*Staphylococcus aureus*) | | |

$^a$lacI gene with single mutation, Gly-187 → Ser (72).
$^b$lacI gene with three mutations, Ala-241 → Thr; Gly-265 → Asp; and Ser-300 → Asn (604).
$^c$The constitutive lpp promoter (P$_{lpp}$) was converted into an inducible promoter by insertion of the lacUV5 propmoter/operator region downstream of P$_{lpp}$. Thus expression occurs only in the presence of a lac inducer (142).
$^d$Wild-type lacI gene.
$^e$cAMP-CAP, cyclic AMP-catabolite activator protein PCR is used to introduce the mutations and construct the complete scFv genes. Once an interesting amino acid in the antibody binding pocket has been chosen, a series of twenty-one different PCR primers are ordered that are complementary to the antibody gene, centered around the amino acid of interest. Each primer is identical except for the codon of the chosen amino acid. *E. coli* preferred codons for the twenty different amino acids and a stop codon (as a control) are used in different PCR reactions. The twenty-one different gene fragments are then incorporated into complete scFV genes using a second step of PCR, the so-called "overlapping" method. As a result, using only PCR, sufficient quantities of all the required scFV gene fragments are produced in twenty-one different vials, each gene identical except of the codon of interest. All of the genetic machinery necessary for the coupled in vitro transcription-translation step is present on the PCR products.

Functional scFV's are produced from the PCR products using coupled in vitro transcription-translation reactions. In twenty-one separate reactions, the PCR products are transcribed into messenger RNA, that is then translated into protein in the same reaction, the so-called "coupled" approach. A preferred embodiment uses the T7 promoter on the gene and thus T7 RNA polymerase to transcribe the message. The inventors used *E. coli* S30 ribosomal extracts for the translation machinery, since this bacterial system has the significant advantage of eliminating the need to cap the message However, it is contemplated that mammalian or plant cell extracts could be used. The twenty-one different vials that started with scFv genes assembled by PCR now contain samples of the corresponding functional scFV's. Importantly, the system is reproducible enough that very similar levels of gene products are produced in each reaction. Thus, no further manipulation or purification is required before the quantitative ELISA analysis.

Without the need for further purification, the protein products from the coupled in vitro transcription-translation step are analyzed quantitatively by ELISA. Both key aspects of scFV binding can be quantitatively investigated using these ELISAs, namely affinity and specificity. Since the concentrations of scFV are similar in each reaction, higher ELISA activity corresponds to higher scFV affinity, and vice versa. Moreover, different antigen analogs may be used to check for binding specificity. Since multiple ELISAs can be run with the product of a single in vitro transcription-translation reaction, desirable binding features of a particular mutant can be identified quickly and precisely. Thus, quantitative information is obtained for all the mutants, allowing for detailed structure-function analyses. Most importantly, since protein structure and function cannot yet be predicted based on amino acid sequence alone, scanning saturation mutagenesis provides the only feasible method to systematically identify antibodies with desirable new properties. Therefore the present invention provides the only method to achieve scanning saturation mutagenesis in a fast, efficient and cost-effective manner.

B. Proteins and Protein Structures of Interest

Proteins generated by methods of the present invention comprise virtually any amino acid sequence as generated from a DNA template. Proteins may be composed of known wild-type sequences or may contain one or more mutations or amino acid substitutions within the amino acid sequence. Proteins also may include one or more amino acid derivatives within their sequence. Each protein is subject to further modification, according to the present invention, to introduce or improve desirable characteristics.

Representative mutant proteins contemplated by the present invention are substitution mutants. Amino acids usually are grouped according to their side chains: simple aliphatic side chains (e.g. glycine, alanine, valine, leucine and isoleucine), aromatic side chains (e.g. phenylalanine, tryptophan, tyrosine, and histidine), oxygen and sulfur containing side chains (e.g. serine, threonine, methionine and cysteine), side chains containing carboxylic or amide groups (e.g. aspartic acid, glutamic acid, asparagine and glutamine), and side chains containing strongly basic groups (e.g. lysine and arginine), and proline. Derivatives of amino acids are also contemplated. An amino acid derivative as used herein is any compound that contains within its structure the basic amino acid core of an a amino-substituted carboxylic acid, with representative examples including azaserine, fluoroalanine, GABA, ornithine, norleucine and cycloserine. These changes will require more detailed manipulations to accomplish.

Certain amino acids may be substituted for other amino acids in a protein structure without appreciable loss of interactive capacity with structures such as, for example, substrate-binding regions. These changes are termed "conservative" in the sense that they preserve the structural and, presumably, required functional qualities of the starting molecule. Conservative amino acid substitutions generally are based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as equivalent.

In making such changes, the hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity, particularly where the polypeptide created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have been devoted to the prediction of secondary structure, and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1988; Wolf et al., 1988), the program PepPlot® (Brutlag et al., 1990; Weinberger et al., 1985), and other new programs for protein tertiary structure prediction (Fetrow & Bryant, 1993).

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan= Trp (W); Tyrosine=Tyr (Y); Valine=Val (V).

Because of the degeneracy of the genetic code, a given polypeptide may be encoded by many nucleic acids. For example, four different three-base codons encode the amino acids alanine, glycine, proline, threonine and valine, while six different codons encode arginine, leucine and serine. Only methionine and tryptophan are encoded by a single codon. A table of amino acids and the corresponding codons is presented herein (Table 2) for use in such embodiments.

TABLE 2

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

In order to generate any nucleic acid encoding a specific polypeptide, one need only refer to the preceding codon table. Substitution of the natural codon with any codon encoding the same amino acid will result in a distinct nucleic acid that encodes a given polypeptide or a variant thereof. As a practical matter, this can be accomplished by the in vitro mutagenesis methodology described herein.

The preceding observations regarding codon selection, site-directed mutagenesis and chemical synthesis apply with equal force to the discussion of substitutional mutants in the section of peptides. Normally, substitutional mutants are generated by site-directed changes in the nucleic acid designed to alter one or more codons of the coding sequence.

Although the present invention is applicable to any protein sequence, proteins which have a convenient assay for activity such as catalytic activity or ligand binding are preferred. As used herein, a ligand is any molecule which binds specifically to a larger one, such as small molecule binding to a protein. Representative examples of target interactions include catalysis, enzyme-substrate interactions, protein-nucleic acid interactions, receptor-ligand interactions, protein-metal interactions and antibody-antigen interactions. Representative target proteins include enzymes, antibodies, cytokines, receptors, DNA binding proteins, chelating agents, and hormones.

In a specific embodiment, an antibody or an antibody fragment is the target protein. The read-out for antibody function generally is binding to an antigen or antigen variant. This aspect of the invention is discussed in greater detail below. As used herein, the term "antibody" or "antibody fragment" is used to refer to any immunologic binding agent such as IgG, IgM, IgA, IgD and IgE, or any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments thereof are well known in the art.

An important aspect of the present invention is the identification of residues that play, or are likely to play, a role in the interaction of interest (e.g., antigen-antibody interaction, metal chelation, receptor binding, substrate binding, etc.). Two primary approaches are envisioned for this identification. First, one may rely on crystal structures of the protein of interest. This information, possibly in combination with a structural analysis of the natural substrate and any enzymatically altered form, should predict the key contact points in the polypeptide. The crystal structure for a large number of proteins now exists and can be accessed through the Brookhaven Protein Database.

Second, as more and more protein sequences become available through sequencing efforts, the ability to predict critical residues in antibodies, enzymes and other active proteins increases dramatically. Over and over, motifs are appearing that serve the same or similar functions in distinct polypeptides. Thus, it will become easier and easier to predict, without any actual experimentation, those residues that contribute to a protein's activity.

C. Antibody Constructs

Antibody and Antibody Fragment Constructs

Any antibody or antibody fragment may be used according to the present invention. However, the preferred construct comprises a single chain antibody format, since no chain association event must take place following the translation. This facilitates the in vitro system for transcription/translation, as discussed and exemplified below. "Antibody" or "antibody fragment" refers to any immunologic binding agent such as IgG, IgM, IgA, IgD and IgE or any antibody-like molecule that has an antigen binding region, and includes antibody fragments such as Fab', Fab, F(ab')$_2$, single domain antibodies (DABs), Fv, scFv (single chain Fv) and the like. The techniques for preparing and using various antibody-based constructs and fragments are well known in the art.

The specificity of an antibody is determined by the complementarity determining regions (CDRs) within the light chain variable regions ($V_L$) and heavy chain variable regions ($V_H$). The $F_{ab}$ fragment of an antibody, which is about one-third the size of a complete antibody contains the heavy and light chain variable regions, the complete light chain constant region and a portion of the heavy chain constant region. $F_{ab}$ molecules are stable and associate well due to the contribution of the constant region sequences. However, the yield of functional $F_{ab}$ expressed in bacterial systems is lower than that of the smaller $F_v$ fragment which contains only the variable regions of the heavy and light chains. The $F_v$ fragment is the smallest portion of an antibody that still retains a functional antigen binding site. The $F_v$ fragment has the same binding properties as the $F_{ab}$, however without the stability conferred by the constant regions, the two chains of the $F_v$ can dissociate relatively easily in dilute conditions.

To overcome this problem, $V_H$ and $V_L$ regions may be fused via a polypeptide linker (Huston et al., 1991) to stabilize the antigen binding site. This single polypeptide $F_v$ fragment is known as a single chain antibody (sc$F_v$). The $V_H$ and $V_L$ can be arranged with either domain first. The linker joins the carboxy terminus of the first chain to the amino terminus of the second chain.

While the present invention has been illustrated with the mutagenesis and in vitro transcription/translation of single chain $F_v$, one of skill in the art will recognize that heavy or light chain $F_v$ or $F_{ab}$ fragments may also be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Antibody and Antibody Fragment Gene Isolation

To accomplish construction of antibodies and antibody fragments, the encoding genes are isolated and identified. The genes can be modified to permit cloning into an expression vector or an in vitro transcription/translation. Although methods can be used such as probing the DNA for $V_H$ and $V_L$ from hybridoma cDNA (Maniatis et al., 1982) or constructing a synthetic gene for $V_H$ and $V_L$ (Barbas et al., 1992), a convenient mode is to use template directed methods to amplify the antibody sequences. A diverse population of antibody genes can be amplified from a template sample by designing primers to the conserved sequences at the 3' and 5' ends of the variable region known as the framework or to the constant regions of the antibody (Iverson et al., 1989). Within the primers, restriction sites can be placed to facilitate cloning into an expression vector. By directing the primers to these conserved regions, the diversity of the antibody population is maintained to allow for the construction of diverse libraries. The specific species and class of antibody can be defined by the selection of the primer sequences as illustrated by the large number of sequences for all types of antibodies given in Kabat et al., 1987, hereby incorporated by reference.

Messenger RNA isolated from the spleen or peripheral blood of an animal can be used as the template for the amplification of an antibody library. In certain circumstances, where it is desirable to display a homogeneous population of antibody fragments on the cell surface, mRNA may be isolated from a population of monoclonal antibodies. Messenger RNA from either source can be prepared by standard methods and used directly or for the preparation of a cDNA template. Generation of mRNA for cloning antibody purposes is readily accomplished by following the well-known procedures for preparation and characterization of antibodies (see, e.g., Antibodies: A Laboratory Manual, 1988; incorporated herein by reference).

Method of Producing Monoclonal Antibodies

Generation of monoclonal antibodies (MAbs) follows generally the same procedures as those for preparing polyclonal antibodies. Briefly, a polyclonal antibody is prepared by immunizing an animal with an immunogenic composition in accordance and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, rabbits are usually preferred for production of polyclonal antibodies.

Immunogenic compositions often vary in immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Recognized means for conjugating a polypeptide to a carrier protein are well known and include glutaraldehyde, m-maleimidobenzoyl-N-hydroxysuccinimide ester, carbodiimides and bis-diazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated, stored and the spleen harvested for the isolation of mRNA from the polyclonal response or the animal can be used to generate MAbs for the isolation of mRNA from a homogeneous antibody population.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g. a small molecule hapten conjugated to a carrier, a purified or partially purified protein, polypeptide or peptide. The immunizing composition is administered in a manner effective to stimulate antibody producing cells. Rodents such as mice and rats are frequently used animals; however, the use of rabbit, sheep frog cells is also possible. The use of rats may provide certain advantages (Goding, pp. 60–61, 1986), but mice are preferred, particularly the BALB/c mouse as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from blood samples. Spleen cells and blood cells are preferable, the former because they are a rich source of antibody-producing cells that are in the dividing plasmablast stage, and the latter because blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al., 1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Simple and rapid assays include radioimmunoassays, enzyme immunoassays, cytotoxicity assays, plaque assays, dot immunobinding assays, and the like.

The selected hybridomas are serially diluted and cloned into individual antibody-producing cell lines from which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Following the isolation and characterization of the desired monoclonal antibody, the mRNA can be isolated using techniques well known in the art and used as a template for amplification of the target sequence.

D. Amplification of a Target Gene Fragment using Enzymatic Polymerization

A number of template dependent processes are available to amplify the target sequences before and after mutagenesis. One of the best known amplification methods is the polymerase chain reaction (referred to as PCR) which is described in detail in U.S. Pat. Nos. 4,683,195, 4,683,202 and 4,800,159, and in Innis et al. (1990), each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of target amplified. Polymerase chain reaction methodologies are well known in the art. Using enzymatic amplification techniques such as PCR, desired control elements may be designed into the primer and thus, will be incorporated into the DNA product.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as an amplification method. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids (Walker et al., 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR) involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having a 3' and 5' sequences of non-specific DNA and middle sequence of specific RNA is hybridized to DNA which is present in a sample. Upon hybridization, the reaction is treated with RNaseH, and the products of the probe identified as distinctive products which are released after digestion. The original template is annealed to another cycling probe and the reaction is repeated.

Other amplification methods are described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Kienow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; O'Hara et al., 1989).

Methods based on ligation of two (or more) oligonucleotides in the presence of nucleic acid having the sequence of the resulting "di-oligonucleotide," thereby amplifying the di-oligonucleotide, also may be used in the amplification step (Wu et al., 1989).

Amplification products may be analyzed by agarose, agarose-acrylamide or polyacrylamide gel electrophoresis using standard methods (see, e.g., Maniatis et al. 1982). For example, one may use a 1% agarose gel stained with ethidium bromide and visualized under UV light. Alternatively, the amplification products may be integrally labeled with radio- or fluorometrically-labeled nucleotides. Gels can then be exposed to x-ray film or visualized under the appropriate stimulating spectra, respectively.

E. Mutagenic Procedures

Mutagenic procedures of the present invention may comprise any mutagenic approach that may be tailored to a particular site in a gene, i.e., site-directed or site-specific mutagenesis. Because the present invention relies on saturation mutagenesis, the present invention contemplates as preferred embodiments those mutagenic procedures that are rapid, efficient and cost effective.

In one embodiment, the mutagenic procedure utilizes chemical synthesis techniques. In so doing, it is possible to exactly place the substitution at one or more particular locations within the gene, and also to specifically define the nature of the alterations. Chemical synthesis methods for DNA are well known within the art. Solid phase techniques are preferred in this regard.

One advantage to the solid phase method of gene synthesis is the opportunity for mutagenesis using combinatorial synthesis techniques. Combinatorial synthesis techniques are defined as those techniques producing large collections or libraries of compounds simultaneously, by sequentially linking different building blocks. Libraries can be constructed using compounds free in solution, but preferably the compound is linked to a solid support such as a bead, solid particle or even displayed on the surface of a microorganism.

Several methods exist for combinatorial synthesis (Holmes et al., 1995; Burbaum et al., 1995; Martin et al., 1995; Freier et al., 1995; Pei et al., 1991; Bruce et al., 1995; Ohlmeyer et al., 1993), including split synthesis or parallel synthesis. Split synthesis may be used to produce small amounts of a relatively large number of compounds, while parallel synthesis will produce larger amounts of a relatively small number of compounds. In general terms, using split synthesis, compounds are synthesized on the surface of a microparticle. At each step, the particles are partitioned into several groups for the addition of the next component. The different groups are then recombined and partitioned to form new groups. The process is repeated until the compound is completed. Each particle holds several copies of the same compound allowing for facile separation and purification. Split synthesis can only be conducted using a solid support.

An alternative technique known as parallel synthesis may be conducted either in solid phase or solution. Using parallel synthesis, different compounds are synthesized in separate receptacles, often using automation. Parallel synthesis may be conducted in microtiter plate where different reagents can be added to each well in a predefined manner to produce a combinatorial library. Parallel synthesis is the preferred approach for use with enzymatic techniques. It is well understood that many modifications of this technique exist and can be adapted for use with the present invention. Using combinatorial methods, a large number of mutant gene templates may be synthesized.

Mutants genes also may be generated by semisynthetic methods known in the art (Barbas et al., 1992). Using the conserved regions of an antibody fragment as a framework, variable regions can be inserted in random combinations one or more at a time to alter the specificity of the antibody fragment and generate novel binding sites, especially in the generation of antibodies to antigens not conducive to immunization such as toxic or labile compounds. Along the same lines, a known antibody sequence may be varied by introducing mutations randomly. This may be accomplished by methods well known in the art such as the use of error-prone PCR.

Using the appropriate oligonucleotide primers, PCR is used for the rapid synthesis of the DNA template containing one or more mutations in the binding protein gene. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In certain applications, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

In a particularly preferred embodiment, overlap PCR is employed as described in FIG. 3A and FIG. 3B and Example 1. Briefly, a plasmid is used as a template for the first round of PCR™, which was carried out under the preferred conditions described in Example 1. The PCR™ products from the first round are purified and used, together with outside primers (Table 2), in the overlap extension PCR™ reaction. The end products contained the site directed replacement of a given amino acid with all other possible amino acid residues.

F. In Vitro Transcription/Translation

The inventors have demonstrated that PCR mutagenesis coupled with synthesis by in vitro transcription-translation and characterization of the protein product by quantitative ELISA can greatly simplify the engineering of polypeptides.

In recent years there has been increased interest in the use of in vitro protein synthesis to produce polypeptides for biochemical studies. Friguet et al (1993) used in vitro translation to generate C-terminal deletions in the β subunit of tryptophan synthase which were then employed to localized the epitope sequences of a panel of monoclonal antibodies. Brand et al (1994) synthesized mutants of the proliferating cell nuclear antigen (CCNA) in vitro to probe for sequences important for the oligomerization of the protein.

However, so far in vitro protein synthesis has not been employed for protein engineering studies. The main reason is that the amount of polypeptide obtained from in vitro transcription/translation is quite small and therefore it is not adequate for rigorous biophysical analysis. However, the protein yield obtained by in vitro synthesis is more than adequate for ligand binding and for determination of function, assuming that a sensitive assay is available. This is particularly important for saturation mutagenesis experiments in which chosen residues are replaced with all of the 20 amino acids. In saturation mutagenesis it is important to identify the amino acid substitutions that abolish protein function. Furthermore, in vitro transcription-translation is ideally suited for identifying amino acid replacements that enhance the protein function.

By integrating PCR mutagenesis, in vitro transcription-translation and functional characterization of the protein products in a microtiter well platform at the inventors have achieved over a ten-fold reduction in time over conventional saturation mutagenesis. With automation, using a robotic station, it is possible to achieve another ten-fold reduction for a total 100-fold reduction in the time and effort required for saturation mutagenesis. This latter reduction will be achieved by increasing the number of samples that are run simultaneously using the robotic system. In this manner, the examination of thousands of amino acid substitutions will finally become a reality and thus open new horizons in protein engineering and protein structure-function studies.

The mutagenized DNA template for the polypeptide of interest can be cloned into a plasmid for in vitro transcription/translation or in the preferred embodiment, the appropriate control elements are included within the PCR product for direct in vitro transcription/translation. In vitro transcription/translation of genes uses cell free extracts to provide the required enzymes, ribosomes and protein factors. The synthesis of proteins is directed by mRNA synthesized from the desired DNA templates. The DNA template must contain the appropriate control elements for the system used including a ribosome binding site and promoter sequence. One of skill in the art would clearly recognize the appropriate required elements for each system.

Prokaryotic in vitro techniques for protein production were the first to be used (Zubay et al., 1970). Subsequently eukaryotic systems were developed using wheat germ (Roberts, 1973) and rabbit reticulocytes (Pelham, 1976). Several new developments have increased the efficiency of these techniques. Examples include, the development of nuclease deficient strains of E. coli to improve the results using linear DNA templates (Yang, 1980) and treatment of reticulocyte lysates with micrococcal nuclease to lower any background expression from the system.

The most recent systems developed for in vitro transcription/translation are based on transcription by phage RNA polymerases including SP6 and SP7 (Krieg, 1987, Studier, 1990). DNA placed under the control of T7 promoter elements can be used as a template for in vitro transcription by T7 RNA polymerase or for complete in vitro transcription/translation with the polymerase added to either a prokaryotic or eukaryotic protein synthesis system. While the methods of the present invention can be used with any in vitro transcription/translation system, the T7 system is preferred for transcription and the use of a prokaryotic translation system is preferred as no capping of the RNA is required.

Using in vitro methods for translation, amino acid derivatives may be incorporated into the protein by addition of the derivatized amino acid to the protein synthesis system mixture. Varying the concentration of the derivatives, with respect to the normal amino acid, permits one to create a mixed population and measure relative effects.

G. Characterization

Mutant polypeptides generated by the present invention may be characterized using a variety of techniques. In general, protein products may be analyzed for the correct apparent molecular weight using SDS-PAGE. This provides an initial indication that the polypeptide was, in fact, synthesized. When compared to the natural molecule, it also indicates whether normal folding or processing is taking place with the mutant. In this regard, it may prove useful to label the polypeptide. Alternatively, the polypeptide may be identified by staining of the gel.

Beyond mere synthesis, proteins may be characterized according to various properties and an extensive range of functions. Properties include isoelectric point, thermal stability, sedimentation rate and folding. One manner of examining folding is the ability to be recognized by a cognate binding partner. The prime example of this function is the antibody-antigen interaction. A wide variety of different immunoassay formats are available for this purpose and are well known in the art. Principally, changes in either affinity or specificity can be determined when the protein is contacted with a specific ligand or panels of related ligands.

Immunoassays can be generally divided into two types: heterogeneous assays requiring multiple separation steps, and homogeneous assays which are performed directly.

Heterogeneous immunoassays in general involve a ligand or antibody immobilized on a solid matrix. A sample containing a ligand is contacted with the immobilized antibody and the amount of complex formed on the matrix support is determined from a label attached directly or indirectly to the immobilized complex. As used in the context of the present invention, ligand is defined as a species that interacts with a non-identical molecule to form a tightly bound, stable complex. For practical purposes, the binding affinity is usually greater than about $10^6$ $M^{-1}$ and is preferably in the range of $10^9$–$10^{15}$ $M^{-1}$. The ligand may be any of several types of organic molecules, including alicyclic hydrocarbons, polynuclear aromatics, halogenated compounds, benzenoids, polynuclear hydrocarbons, nitrogen heterocyclics, sulfur heterocyclics, oxygen heterocyclics, and alkane, alkene alkyne hydrocarbons, etc. Biological molecules are of particular interest, including amino acids, peptides, proteins, lipids, saccharides, nucleic acids and combinations thereof. Of course it will be understood that these are by way of example only and that contemplated immunoassay methods are applicable to detecting an extraordinarily wide range of compounds, so long as one can obtain an antibody that binds with the ligand of interest.

Heterogeneous immunoassays may be performed as sandwich assays in which a molecule of interest is reacted with an immobilized antibody that specifically binds that molecule with high affinity. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of ligand in the sample, is measured.

Detection of immunocomplex formation is well known in the art and may be achieved through the application of numerous approaches. These approaches are typically based upon the detection of a label or marker, such as any of the radioactive, fluorescent, chemiluminescent, electrochemiluminescent, biological or enzymatic tags or labels known in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

Preferred methods for detection includes radioimmunoassay (RIA) or enzyme-linked immunosorbent assay (ELISA) with ELISA being most preferred due to generally increased sensitivity. ELISAs are extensively used in biotechnology applications, particularly as immunoassays for a wide range of antigenic substances. The sensitivity of ELISA is based on the enzymatic amplification of the signal Other preferred proteins contemplated for use in accordance with the present invention are those which have a convenient assay for activity. Representative examples of target interactions include catalysis, enzyme-substrate interactions, protein-nucleic acid interactions, receptor-ligand interactions and protein-metal interactions. In these assays the mutant proteins can be compared with the wild-type protein for changes in the ability to perform any of the foregoing functions.

As used herein, the term "contacting" is defined as bringing the reaction components into close enough proximity to each other to allow the desired interaction to occur. Contacting may be accomplished by mixing the components in solution, for example, or by heterogeneous interaction such as by flow contact through a column or immobilizing matrix that binds to one of the components.

For mutant proteins having a catalytic activity, the appropriate reaction may be monitored for a change in catalytic rate or an alteration in specificity.

H. Examples

The following examples are included to demonstrate preferred embodiments of the invention. It should be appreciated by those of skill in the art that the techniques disclosed in the examples which follow represent techniques discovered by the inventors to function well within the practice of the invention, and thus can be considered to constitute preferred modes for of practice. However, those of skill in the art should, in light of the present disclosure, appreciate that many changes can be made in the specific embodiments which are disclosed and still obtain a like or similar result without departing from the spirit and scope of the invention.

EXAMPLE 1

Experimental

Materials

Taq polymerase was purchased from Promega (Madison, Wis.), dNTPs from Pharmacia (Uppsala, Sweden), and oligonucleotide primers from Midland Certified Reagent (Midland, Tex.). Pyruvate kinase, tRNA, and nucleotide triphosphates were obtained from Boehringer Mannheim (Indianapolis, Ind.). Digoxin and digitoxin were purchased from Sigma (St. Louis, Mo.). Ouabain was purchased from Fluka (Ronkonkoma, N.Y.). 3-aminodeoxydigoxigenin hemisuccinimide was purchased from Molecular Probes (Eugene, Oreg.). Pfu DNA polymerase was purchased from Stratagene (La Jolla, Calif.). The BIAcorc 1000 and reagents including sensor chip CM5, the amine coupling kit containing N-hydroxysuccinmide (NHS), N-ethyl-N'-(3-diethylaminopropyl)carbodiimide (EDC), and ethanolamine hydrochloride were obtained from Pharmacia Biosensor AB (Uppsala, Sweden).

PCR™ Mutagenesis

Mutations in the scFv(digoxin) antibody were generated by the overlapping PCR™ method (Ho et al., 1989; Horton and Pease, 1991; Higuchi et al., 1988) as depicted in FIG. 3A. Briefly, the plasmid pET25b(scFv(Dig)) SEQ ID NO: 1 (Burks and Iverson, 1995) was used as a template for PCR™ (SEQ ID NO:132 represents the amino acid sequence encoded by SEQ ID NO:1). For the first round PCR™, a 2 Kb-Nde I-Pvu I fragment from pET25b(scFv(Dig)) was used as the 3' template, whereas a 4 Kb, XhoI-Pvu I fragment was used as the 5' template. The restriction fragments were isolated on an agarose gel to eliminate the possibility that any contaminating full-length, wild-type scFv(Dig) construct was present. A list of the primers used for the first and second PCR™ steps are included in the Table 2.

First round PCR™ was carried out in 50 mM KCl, 10 mM Tris-HCl pH 9.0 (25° C.) 0.1% Triton X-100, 0.2 mM dNTP's, 2.5 units Taq polymerase (Promega), 0.6 μM each of the two primers and 0.05 μg template in 100 μl total volume. Amplification was carried out using the following sequence: one cycle at 94° C. for 2 min; 29 cycles consisting of 94° C. for 1 min, 55° C. 2 min, and 72° C. for 3 min; one cycle of 94° C. for 1 min, 55° C. for 2 min and 72° C. for 10 min.

The PCR™ products from the first round were gel purified and used, together with outside primers (Table 2), in the overlap extension PCR™ reaction. For this round of PCR™, the mix contained 50 mM KCl, 10 mM Tris0HCl pH 9.0 (25° C.) 0.1% Triton X-100, 0.2 mM dNTP's, 2.5 units Taq polymerase (Promega), 0.6 μM each of the two primers and 0.05 μg each of both the 5'-template and the 3'-template in 100 μl total volume. The amplification sequence for the overlap extension reaction was the same as for the first round reactions except that the annealing temperature for the first 5 cycles was set between 48° C. and 55° C., depending on the Tm of overlapping sequence. The PCR™ products were ethanol precipitated and the pellets were resuspended in 100 μl water.

TABLE 2

Complete sequences for the sets of PCR™ primers used to construct the different mutant scFv(Dig) constructs.

| | | |
|---|---|---|
| H:33 SITE | | |
| H:33 OVERLAP PRIMER | 5'-CGGTGAAAATGTACCCTG-3' | (SEQ ID ND:2) |
| TYR | 5'-CAGGGTACATTTTCACCGACTTCTACATGAATTGGG-3' | (SEQ ID NO:3) |
| ALA | 5'-CAGGGTACATTTTCACCGACTTCGCAATGAATTGGG-3' | (SEQ ID NO:4) |
| ARG | 5'-CAGGGTACATTTTCACCGACTTCCGTATGAATTGGG-3 | (SEQ ID NO:5) |
| ASN | 5'-CAGGGTACATTTTCACCGACTTCAACATGAATTGGG-3 | (SEQ ID NO:6) |
| ASP | 5'-CAGGGTACATTTTCACCGACTTCGACATGAATTGGG-3 | (SEQ ID NO:7) |
| CYS | 5'-CAGGGTACATTTTCACCGACTTCTGCATGAATTGGG-3 | (SEQ ID NO:8) |
| GLU | 5'-CAGGGTACATTTTCACCGACTTCGAAATGAATTGGG-3 | (SEQ ID ND:9) |
| GLN | 5'-CAGGGTACATTTTCACCGACTTCCAGATGAATTGGG-3 | (SEQ ID NO:10) |
| GLy | 5'-CAGGGTACATTTTCACCGACTTCGGCATGAATTGGG-3 | (SEQ ID NO:11) |
| HIS | 5'-CAGGGTACATTTTCACCGACTTCCACATGAATTGGG-3 | (SEQ ID NO:12) |
| ILE | 5'-CAGGGTACATTTTCACCGACTTCATCATGAATTGGG-3 | (SEQ IO NO:13) |
| LEU | 5'-CAGGGTACATTTTCACCGACTTCCTGATGAATTGGG-3 | (SEQ ID ND:14) |
| LYS | 5'-CAGGGTACATTTTCACCGACTTCAAAATGAATTGGG-3 | (SEQ ID NO:15) |
| MET | 5'-CAGGGTACATTTTCACCGACTTCATGATGAATTGGG-3 | (SEQ ID NO:16) |
| PHE | 5'-CAGGGTACATTTTCACCGACTTCTTCATGAATTGGG-3 | (SEQ ID NO:17) |
| PRO | 5'-CAGGGTACATTTTCACCGACTTCCCGATGAATTGGG-3 | (SEQ ID ND:18) |
| SER | 5'-CAGGGTACATTTTCACCGACTTCTCCATGAATTGGG-3 | (SEQ ID NO:19) |
| THR | 5'-CAGGGTACATTTTCACCGACTTCACCATGAATTGGG-3 | (SEQ ID NO:20) |
| TRP | 5'-CAGGGTACATTTTCACCGACTTCTGGATGAATTGGG-3 | (SEQ ID NO:21) |
| VAL | 5'-CAGGGTACATTTTCACCGACTTCGTTATGAATTGGG-3 | (SEQ ID NO:22) |
| DOUBLE STOP CODON | 5'-CAGGGTACATTTTCACCTGATTCTGAATGAATTGGG-3 | (SEQ ID NO:23) |
| H:35 SITE: | | |
| H:35 OVERLAP PRIMER | 5'-GTAGAAGTCGGTGAAAATGT -3 | (SEQ ID NO:24) |
| ALA | 5'-ACATTT TCACCGACT TCTACATGGCATGGGTTCGC-3 | (SEQ ID NO:25) |
| ARG | 5'-ACATTT TCACCGACT TCTACATGCGTTGGGTTCGC-3 | (SEQ ID NO:26) |
| ASN | 5'-ACATTT TCACCGACT TCTACATGAACTGGGTTCGC-3 | (SEQ ID NO:27) |
| ASP | 5'-ACATTT TCACCGACT TCTACATGGACTGGGTTCGC-3 | (SEQ ID ND:28) |
| CYS | 5'-ACATTT TCACCGACT TCTACATGTGCTGGGTTCGC-3 | (SEQ ID NO:29) |
| GLN | 5'-ACATTT TCACCGACT TCTACATGGAATGGGTTCGC-3 | (SEQ ID NO:30) |
| GLU | 5'-ACATTT TCACCGACT TCTACATGCAGTGGGTTCGC-3 | (SEQ ID NO:31) |
| GLY | 5'-ACATTT TCACCGACT TCTACATGGGCTGGGTTCGC-3 | (SEQ ID NO:32) |
| HIS | 5'-ACATTT TCACCGACT TCTACATGCACTGGGTTCGC-3 | (SEQ IO NO:33) |
| ILE | 5'-ACATTT TCACCGACT TCTACATGATCTGGGTTCGC-3 | (SEQ ID NO:34) |
| LEU | 5'-ACATTT TCACCGACT TCTACATGCTGTGGGTTCGC-3 | (SEQ ID NO:35) |
| LYS | 5'-ACATTT TCACCGACT TCTACATGAAATGGGTTCGC-3 | (SEQ ID NO:36) |
| MET | 5'-ACATTT TCACCGACT TCTACATGATGTGGGTTCGC-3 | (SEQ ID NO:37) |

TABLE 2-continued

Complete sequences for the sets of PCR™
primers used to construct the different mutant scFv(Dig) constructs.

| | | |
|---|---|---|
| PHE | 5'-ACATTT TCACCGACT TCTACATGTTCTGGGTTCGC-3 | (SEQ ID NO:38) |
| PRO | 5'-ACATTT TCACCGACT TCTACATGCCGTGGGTTCGC-3 | (SEQ ID NO:39) |
| SER | 5'-ACATTT TCACCGACT TCTACATGTCCTGGGTTCGC-3 | (SEQ ID NO:40) |
| THR | 5'-ACATTT TCACCGACT TCTACATGACCTGGGTTCGC-3 | (SEQ ID Na:41) |
| TRP | 5'-ACATTT TCACCGACT TCTACATGTGGTGGGTTCGC-3 | (SEQ ID NO:42) |
| TYR | 5'-ACATTT TCACCGACT TCTACATGTACTGGGTTCGC-3 | (SEQ ID NO:43) |
| VAL | 5'-ACATTT TCACCGACT TCTACATGGTTTGGGTTCGC-3 | (SEQ ID NO:44) |
| DOUBLE STOP CODON | 5'-ACATTT TCACCGACT TCTACTGATGATGGGTTCGC-3 | (SEQ ID NO:45) |

H:50 SITE

| | | |
|---|---|---|
| H:50 OVERLAP PRIMER | 5'-TCCCCATATTCTGGGGTTAC-3 | (SEQ ID NO:46) |
| TYR | 5'-AGCCGGTAACCCCAGAATATGGGGAAATGTACCCGATGTAGTCTAG-3' | (SEQ ID NO:47) |
| ALA | 5'-AGCCGGTAACCCCAGAATATGGGGAAATTGCCCCGATGTAGTCTAG-3' | (SEQ ID NO:48) |
| ARG | 5'-AGCCGGTAACCCCAGAATATGGGGAAATACGCCCGATGTAGTCTAG-3' | (SEQ ID NO:49) |
| ASN | 5'-AGCCGGTAACCCCAGAATATGGGGAAATGTTCCCGATGTAGTCTAG-3' | (SEQ ID NO:50) |
| ASP | 5'-AGCCGGTAACCCCAGAATATGGGGAAATGTCCCGATGTAGTCTAG-3' | (SEQ ID NO:51) |
| CYS | 5'-AGCCGGTAACCCCAGAATATGGGGAAATGCACCCGATGTAGTCTAG-3' | (SEQ ID NO:52) |
| GLN | 5'-AGCCGGTAACCCCAGAATATGGGGAAATTTCCCCGATGTAGTCTAG.3' | (SEQ ID NO:53) |
| GLU | 5'-AGCCGGTAACCCCAGAATATGGGGAAATCTGCCCGATGTAGTCTAG-3' | (SEQ ID NO:54) |
| GLY | 5'-AGCCGGTAACCCCAGAATATGGGGAAATGCCCCGATGTAGTCTAG-3' | (SEQ ID NO:55) |
| HIS | 5'-AGCCGGTAACCCCAGAATATGGGGAAATGTGCCCGATGTAGTCTAG-3' | (SEQ ID NO:56) |
| ILE | 5'-AGCCGGTAACCCCAGAATATGGGGAAATGATCCCGATGTAGTCTAG-3' | (SEQ ID NO:57) |
| LEU | 5'-AGCCGGTAACCCCAGAATATGGGGAAATCAGCCCGATGTAGTCTAG-3' | (SEQ ID NO:58) |
| LYS | 5'-AGCCGGTAACCCCAGAATATGGGGAAATTTTCCCGATGTAGTCTAG-3' | (SEQ ID NO:59) |
| MET | 5'-AGCCGGTAACCCCAGAATATGGGGAAATCATCCCGATGTAGTCTAG-3' | (SEQ ID NO:60) |
| PHE | 5'-AGCCGGTAACCCCAGAATATGGGGAAATGAACCCGATGTAGTCTAG-3' | (SEQ ID NO:61) |
| PRO | 5'-AGCCGGTAACCCCAGAATATGGGGAAATCGGCCCGATGTAGTCTAG.3' | (SEQ ID NO:62) |
| SER | 5'-AGCCGGTAACCCCAGAATATGGGGAAATGGACCCGATGTAGTCTAG-3' | (SEQ ID ND:63) |
| THR | 5'-AGCCGGTAACCCCAGAATATGGGGAAATGGTCCCGATGTAGTCTAG-3' | (SEQ ID NO:64) |
| TRP | 5'-AGCCGGTAACCCCAGAATATGGGGAAATCCACCCGATGTAGTCTAG-3' | (SEQ ID NO:65) |
| VAL | 5'-AGCCGGTAACCCCAGAATATGGGGAAATAACCCGATGTAGTCTAG-3' | (SEQ ID NO:66) |
| DOUBLE STOP CODON | 5'-AGCCGGTAACCCCAGAATATGGGATCATCACCCGATGTAGTCTAG-3' | (SEQ ID NO:67) |

H:100 SITE

| | | |
|---|---|---|
| H:100 OVERLAP PRIMER | 5'-GGATTATTGGGGTCATGGTGCTA-3' | (SEQ ID NO:68) |
| ALA | 5'-AGCACCATGACCCCAATAATCCATGGCTGCTTTGTTACC -3' | (SEQ ID NO:69) |
| ARG | 5'-AGCACCATGACCCCAATAATCCATGGCACGTTTGTTACC -3' | (SEQ ID NO:70) |
| ASN | 5'-AGCACCATGACCCCAATAATCCATGGCGTTTTGTTACC -3' | (SEQ ID NO:71) |

TABLE 2-continued

Complete sequences for the sets of PCR™ primers used to construct the different mutant scFv(Dig) constructs.

| | | |
|---|---|---|
| ASN | 5'-AGCACCATGACCCCAATAATCCATGGCGTCTTTGTTACC-3' | (SEQ ID NO:72) |
| CYS | 5'-AGCACCATGACCCCAATAATCCATGGCGCATTTGTTACC -3' | (SEQ ID NO:73) |
| GLN | 5'-AGCACCATGACCCCAATAATCCATGGCTTCTTTGTTACC -3' | (SEQ ID NO:74) |
| GLU | 5'-AGCACCATGACCCCAATAATCCATGGCCTGTTTGTTACC -3' | (SEQ ID ND:75) |
| GLY | 5'-AGCACCATGACCCCAATAATCCATGGCGCCTTTGTTACC -3' | (SEQ ID NO:76) |
| HIS | 5'-AGCACCATGACCCCAATAATCCATGGCGTGTTTGTTACC -3' | (SEQ ID NO:77) |
| ILE | 5'-AGCACCATGACCCCAATAATCCATGGCGATTTTGTTACC -3' | (SEQ ID NO:78) |
| LEU | 5'-AGCACCATGACCCCAATAATCCATGGCCAGTTTGTTACC -3' | (SEQ ID NO:79) |
| LYS | 5'-AGCACCATGACCCCAATAATCCATGGCTTTTTTGTTACC -3' | (SEQ ID NO:80) |
| MET | 5'-AGCACCATGACCCCAATAATCCATGGCCATTTTGTTACC -3' | (SEQ ID NO:81) |
| PHE | 5'-AGCACCATGACCCCAATAATCCATGGCGAATTTGTTACC -3' | (SEQ ID NO:82) |
| PRO | 5'-AGCACCATGACCCCAATAATCCATGGCCGGTTTGTTACC-3' | (SEQ ID NO:83) |
| SER | 5'-AGCACCATGACCCCAATAATCCATGGCGGATTTGTTACC -3' | (SEQ ID NO:84) |
| THR | 5'-AGCACCATGACCCCAATAATCCATGGCGGTTTTGTTACC -3' | (SEQ ID NO:85) |
| TRP | 5'-AGCACCATGACCCCAATAATCCATGGCCCATTTGTTACC -3' | (SEQ ID NO:86) |
| TYR | 5'-AGCACCATGACCCCAATAATCCATGGCGTATTTGTTACC -3' | (SEQ ID NO:87) |
| VAL | 5'-AGCACCATGACCCCAATAATCCATGGCAACTTTGTTACC -3' | (SEQ ID NO:88) |
| DOUBLE STOP CODON | 5'-AGCACCATGACCCCAATAATCCATTCATCATTTGTTACC -3' | (SEQ ID NO:89) |
| L:94 SITE | | |
| L:94 AND L:96 OVERLAP PRIMER | 5'-GCGTAGTTTGGCTACAGT-3' | (SEQ ID NO:90) |
| WILD-TYPE L:VAL94 L:PRO96 | 5'-AGCCAAACTACGCATGTTCCACCCACGTTCG-3' | (SEQ ID NO:91) |
| ALA | 5'-AGCCAAACTACGCATGCACCACCCACGTTCG-3' | (SEQ ID NO:92) |
| ARG | 5'-AGCCAAACTACGCATCGTCCACCCACGTTCG-3' | (SEQ ID NO:93) |
| ASN | 5'-AGCCAAACTACGCATAACCCACCCACGTTCG-3' | (SEQ ID NO:94) |
| ASP | 5'-AGCCAAACTACGCATGACCCACCCACGTTCG-3' | (SEQ ID NO:95) |
| CYS | 5'-AGCCAAACTACGCATTGCCCACCCACGTTCG-3' | (SEQ ID NO:96) |
| GLU | 5'-AGCCAAACTACGCATGAACCACCCACGTTCG-3' | (SEQ ID NO:97) |
| GLN | 5'-AGCCAAACTACGCATCAGCCACCCACGTTCG-3' | (SEQ ID NO:98) |
| GLY | 5'-AGCCAAACTACGCATGGCCCACCCACGTTCG-3' | (SEQ ID NO:99) |
| HIS | 5'-AGCCAAACTACGCATCACCCACCCACGTTCG-3' | (SEQ ID NO:100) |
| ILE | 5'-AGCCAAACTACGCATATCCCACCCACGTTCG-3' | (SEQ ID NO:101) |
| LEU | 5'-AGCCAAACTACGCATCTGCCACCCACGTTCG-3' | (SEQ ID NO:102) |
| LYS | 5'-AGCCAAACTACGCATAAACCACCCACGTTCG-3' | (SEQ ID NO:103) |
| MET | 5'-AGCCAAACTACGCATATGCCACCCACGTTCG-3' | (SEQ ID NO:104) |
| PHE | 5'-AGCCAAACTACGCATTTCCCACCCACGTTCG-3' | (SEQ ID NO:105) |
| PRO | 5'-AGCCAAACTACGCATCCGCCACCCACGTTCG-3' | (SEQ ID NO:106) |

TABLE 2-continued

Complete sequences for the sets of PCR™ primers used to construct the different mutant scFv(Dig) constructs.

| SER | 5'-AGCCAAACTACGCATTCCCCACCCACGTTCG-3' | (SEQ ID NO:107) |
| THR | 5'-AGCCAAACTACGCATACCCCACCCACGTTCG-3' | (SEQ ID NO:108) |
| TRP | 5'-AGCCAAACTACGCATTGGCCACCCACGTTCG-3' | (SEQ ID NO:109) |
| DOUBLE STOP CODON | 5'-AGCCAAACTACGCATTGACCATGAACGTTCG-3' | (SEQ ID NO:110) |

L:96 SITE

| ALA | 5'-AGCCAAACTACGCATGTTCCAGCAACGTTCG-3' | (SEQ ID NO:111) |
| ARG | 5'-AGCCAAACTACGCATGTTCCACGTACGTTCG-3' | (SEQ ID NO:112) |
| ASN | 5'-AGCCAAACTACGCATGTTCCAAACACGTTCG-3' | (SEQ ID NO:113) |
| ASP | 5'-AGCCAAACTACGCATGTTCCAGACACGTTCG-3' | (SEQ ID NO:114) |
| CYS | 5'-AGCCAAACTACGCATGTTCCATGCACGTTCG-3' | (SEQ ID NO:115) |
| GLU | 5'-AGCCAAACTACGCATGTTCCAGAAACGTTCG-3' | (SEQ ID NO:116) |
| GLN | 5'-AGCCAAACTACGCATGTTCCACAGACGTTCG-3' | (SEQ ID NO:117) |
| GLY | 5'-AGCCAAACTACGCATGTTCCAGGCACGTTCG-3' | (SEQ ID NO:118) |
| HIS | 5'-AGCCAAACTACGCATGTTCCACACCGTTCG-3' | (SEQ ID NO:119) |
| ILE | 5'-AGCCAAACTACGCATGTTCCAATCACGTTCG-3' | (SEQ ID NO:120) |
| LEU | 5'-AGCCAAACTACGCATGTTCCACTGACGTTCG-3' | (SEQ ID NO:121) |
| LYS | 5'-AGCCAAACTACGCATGTTCCAAAAACGTTCG-3' | (SEQ ID NO:122) |
| MET | 5'-AGCCAAACTACGCATGTTCCAATGACGTTCG-3' | (SEQ ID NO:123) |
| PHE | 5'-AGCCAAACTACGCATGTTCCATTCACGTTCG-3' | (SEQ ID NO:124) |
| SER | 5'-AGCCAAACTACGCATGTTCCATCCACGTTCG-3' | (SEQ ID NO:125) |
| THR | 5'-AGCCAAACTACGCATGTTCCAACCACGTTCG-3' | (SEQ ID NO:126) |
| TRP | 5'-AGCCAAACTACGCATGTTCCATGGACGTTCG-3' | (SEQ ID NO:127) |
| TYR | 5'-AGCCAAACTACGCATGTTCCATACACGTTCG-3' | (SEQ ID NO:128) |
| VAL | 5'-AGCCAAACTACGCATGTTCCAGTTACGTTCG-3' | (SEQ ID NO:129) |

PRIMERS OF T7 PROMOTER AND TERMINATDR

| 5'-PRIMER | 5'-CGATGCGTCCGGCGTAGA-3' | (SEQ ID NO:130) |
| 3'-PRIMER | 5'-GCTAGTTATTGCTCAGCGG-3' | (SEQ ID NO:131) |

In Vitro Transcription/Translation

In vitro protein synthesis using an *E. coli* coupled transcription/translation system was carried out essentially as described (Kudlicki et al., 1994) and as outlined in FIG. 3B. T7 RNA polymerase and S30 *E. coli* extract for coupled transcription/translation were prepared using standard procedures (Kudlicki et al., 1994; Burks, 1996).

The coupled transcription/translation reactions were carried out in 30 µl total volume and the reaction mix contained the following: 55 mM Tris-acetate, pH 7.8, 2 mM DTT, 1.2 mM ATP, 0.8 mM CTP, 0.8 mM GTP, 0.8 mM UTP, 2% polyethylene glycol (M.W. 8,000), 27 mM phosphoenol pyruvate, 0.4 mM cAMP, 35 µg/ml folinic acid, 30 mM ammonium acetate, 72 mM KOAc, 1.5 mM Ca(OAc)$_2$, 0.35 mM of each amino acid, 0.5 mM EDTA, 0.3 mM glucose-6-phosphate, 2 µg T7 RNA polymerase, 0.4 µg pyruvate kinase, 20 µg t-RNA, 5 µg rifampicin, 13.3 mM Mg(OAc)$_2$ and 5 µl of *E. coli* S30 fraction. Reactions were initiated by adding 0.5 µg of the DNA produced by overlap extension in 7 µl.

For radiolabelling of the protein synthesis products 0.083 mM of $^{35}$S-Methionine (1175 Ci/mmole, New England Nuclear, Boston Mass.), was added to the reaction mixture. Reactions were incubated for 25 min at 37° C. with gentle shaking and were stopped by placing on ice. SDS-PAGE using in 15% polyacrylamide gels (Laemmli, 1970) and autoradiography was used to analyze the protein products.

ELISA Screening

Antibody capture ELISA was performed using standard procedures (Harlow and Lane, 1988). The digoxin-BSA, digitoxin-BSA and ouabain-BSA conjugates used in the ELISA analysis were prepared via oxidization of the terminal sugar residues with $NaIO_4$ followed by covalent attachment to BSA through reductive amination in the presence of $NaBH_4$ (Smith et al., 1970). The digoxigenin-BSA conjugate was prepared from a direct reaction between BSA and 3-aminodeoxydigoxigenin hemisuccinimide (Molecular Probes, Inc. Eugene, Oreg.) according to the manufacturer's instructions.

Microtiter plates were coated with 50 µl per well of hapten-conjugated BSA, at a concentration of 4 mg/ml and incubated at 4° C. for at least 18 hours. Prior to use, the plates were washed three times with PBS [140 mM NaCl, 2.7 mM KCl, 10 mM $Na_2HPO_4.7H_2O$, 1.8 m$MKH_2PO_4$]. Non-specific binding was blocked by coating with 5% w/v boiled powdered milk (Carnation) in PBS for 2 hours at room temperature followed by four washes with PBS alone. Aliquots from the transcription/translation reactions were diluted to a total of 50 µl with a solution of 1% w/v boiled powdered milk in PBS and incubated at room temperature overnight. After three washes with PBS, the plates were incubated for 1 hour at room temperature with 50 µl of a 0.28 µg/ml of a murine monoclonal anti-HSV IgG Novagen (Madison, Wis.) in 1% w/v boiled powdered milk/PBS. Unbound antibody was removed by washing the plates three times with PBS and then incubated with the secondary antibody solution (50 µl per well of 0.2 mg/ml goat anti-mouse IgG(H+L) conjugated to horseradish peroxidase (Pierce, Rockford, Ill.) diluted 1:500 in 1% w/v powdered milk/PBS). The plates were washed three times and were developed with the calorimetric horseradish peroxidase substrate 2,2'-azine-bis(3-ethylbenzothiazoline)-6-sulfonic acid diammonium salt (ABTS) (Pierce, Rockford, Ill.). The absorbance of each well of the ELISA plates was measured at 405 nm on a microplate autoreader when the ABTS reaction was still in the linear range, a fact that was confirmed by taking several time points per plate.

For each cardiac glycoside being investigated (digoxin, digitoxin, digoxigenin, ouabain), the absorbances for each mutant were linearly scaled to that of the wild-type scFv (Dig), which was assigned a value of 1.0, then plotted in the histograms (FIGS. 2A–2F). Wild-type scFv(Dig) was included on every ELISA plate to provide an internal calibration for results obtained on different plates. Truncated scFv(Dig) polypeptides generated by stop codon insertion exhibited no hapten binding and were thus used to establish the baseline in the ELISA assays.

Expression and Purification of scFvs

Single chain Fv mutants were produced and purified according to Burks (Burks and Iverson, 1995). The scFv genes from second round overlap extension PCR were ligated into pET25b plasmid and transformed into *E. Coli* BL21 (DE3) strain. Inclusion bodies that consist of scFvs were isolated from cell lysates and dissolved in 8 M urea. Soluble scFvs were purified by a metal chelating column (IMAC) and refolded by dialyzing against Tris buffer (50 mM Tris. HCl, pH 7.4, 500 mM KCl, 10% glycerol). Protein concentrations were determined by $OD_{280}$ (Σ=44850) (Pace et al., 1995; Nieba et al., 1989). For the kinetics measurement, antibodies were further purified by a size exclusion gel filtration column Sepharose-75 (Pharmacia Biosensor AB, Sweden) to remove any dimeric or polymeric proteins.

Surface Plasmon Resonance (SPR) Measurement of Single Chain Antibody Mutants

The digoxin-BSA, digitoxin-BSA, digoxigenin-BSA and ouabain-BSA conjugates were immobilized on the surface of a sensor chip CM5 (approximately 400 RU) following the standard protocol from Pharmacia Biosensor. All kinetics experiments were performed in buffer containing 150 mM NaCl, 10 mM HEPES, 3.4 mM EDTA, and 0.005% P20, pH 7.4 at 25° C. with a flowrate of 60 µl/min (Myszka et al., 1997; Zeder-Lutz et al., 1997; Oddie et al., 1997). ScFv proteins over the concentration range of 25 nM to 400 nM were added to the chip for the association rate measurements. To prevent the rebinding of antibodies on the chip surface, soluble haptens (up to 1 mM) were added into elution buffer for the dissociation rate measurements (Schier et al., 1996). The antibody bound chip was regenerated by 50% ethylene glycol, pH 10. The values of association and dissociation rate of antibodies were calculated using BIAevaluation software from Pharmacia Biosensor. $k_{on}$ was determined from a plot of $(\ln(dR/dt))/t$ versus concentration (Karlson et al., 1991). $k_{off}$ was determined from a plot of $\ln(Ro/R)$ versus time.

Amino Acid Index Analysis

The amino acid index database, more than 402 different amino acid indices corresponding to the different properties of amino acid, have been retrieved through the internet (Tomi and Kanehisa, 1996). Normalized ELISA data was plotted vs amino acid index in an effort to establish any general trends.

EXAMPLE 2

Initial Results

Figure 1:
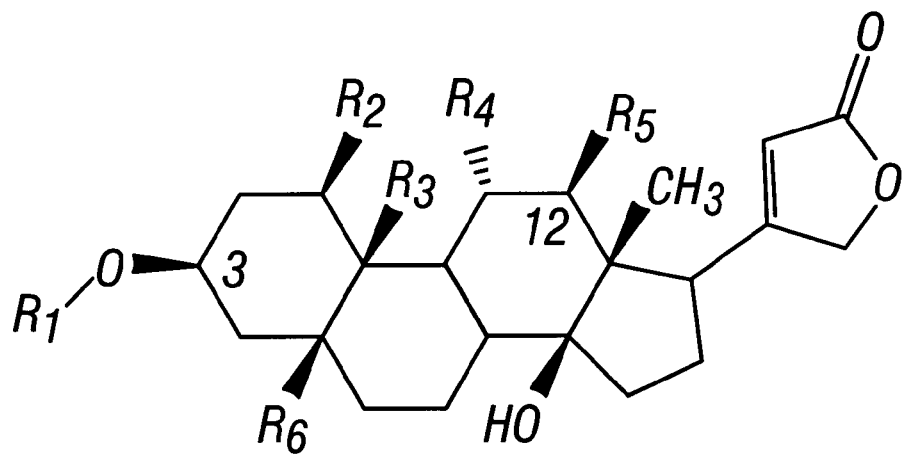
FIG. 1. Structures of digoxin and the three analogs used in the present studies.

An example of an antibody system for which the in vitro scanning saturation mutagenesis system may be used is the high affinity anti-digoxin single chain Fv (scFv(Dig)) (Huston et al., 1988; Burks and Iverson, 1995; Francisco et al., 1993) derived from the well-studied anti-digoxin 26-10 murine monoclonal antibody (Mudgett-Hunter et al., 1982). Studies have shown that the 26-10 antibody binds to the cardiac glycosides digoxin, digitoxin and digoxigenin with high affinity ($K_a$ approximately $9 \times 10^9$ M$^{-1}$) and with a 42-fold lower affinity to ouabain (Schildbach et al., 1993). Digoxin and related cardiac glycosides (FIG. 1) consist of a 5β, 14β-steroid body, linked to an α,β-unsaturated lactone at C17 and an O-linked carbohydrate at position 3. The three-dimensional structure of the 26-10 Fab complexed with digoxin (Jeffery et al., 1993) reveals that the 3'-tridigitoxose is exposed to the solvent whereas the lactone ring is fully buried at the bottom edge of the binding site. Unlike other antibody-antigen complexes (Braden and Poljak, 1995), binding of digoxin to 26-10 Fab does not appear to cause detectable conformational changes of either the antibody or the hapten. Both affinity and specificity are derived entirely from shape complementarity as no hydrogen bonds have been identified between digoxin and the antibody.

Initially, six residues chosen for study, namely H:Tyr33, H:Asn35, H:Tyr50, H:Trp100, L:Val94 and L:Pro96 (wherein the H and L designations refer to residues of the heavy chain and light chain, respectively) consist of three aromatic residues that define the largely hydrophobic walls of the binding pocket and thereby make extensive Van der Waals contact with hapten (heavy chain residues H:Tyr33, H:Tyr50 and H:Trp100), a residue that forms hydrogen bonds with contact residues and therefore is presumably of importance in maintaining the architecture of the binding pocket (H:Asn35) and, finally, two residues that define the bottom of the binding pocket (light chain residues L:Val94 and L:Pro96). In an expanded study, two more aromatic residues (H:Tyr47 and H:Met100b), an additional hydrogen bond forming residue (H:Ser95) and an additional light chain residue that defines the bottom of the binding pocket (L:Thr91) also were characterized.

For each chosen residue, in vitro scanning saturation mutagenesis was carried out. Briefly, at each site, twenty-one genes encoding all possible amino acid substitutions as well as a double stop codon (control) were constructed by overlap extension PCR. The final products of the overlap extension PCR reaction contain a T7 promoter and ribosome binding site in front of the scFv gene. An HSV sequence is also present at the C-terminal end of the scFv gene, so that the scFv protein can be detected by ELISA using an anti-HSV monoclonal antibody. The PCR overlap extension products were used as templates for coupled in vitro transcription-translation reactions to produce functional scFv proteins. An *E. coli* S30 ribosomal extract, as opposed to mammalian or plant cell extracts, was used for in vitro translation.

The protein products from the coupled in vitro transcription-translation step were analyzed by ELISA. In the ELISA assays, 96-well microtiter plates were coated with the BSA conjugate of digoxin, digitoxin, digoxigenin, or ouabain. The microtiter plates were then incubated with equal amounts from each of the in vitro synthesis reactions. In order to provide accurate calibration, the construct prepared with the wild-type sequence was used on each ELISA plate. It should be noted that the wild-type construct was produced by the overlapping PCR method alongside the mutants, thereby providing an accurate calibration for all stages of the procedure. The ELISA results for the different mutants binding to digoxin and the three analogs (760 relative affinity values in all) were recorded.

The single chain Fv form (scFv(Dig)) of the 26-10 antibody was used since the presence of only one polypeptide chain eliminates chain association difficulties that are possible with Fab antibodies. In the initial studies a total of 114 mutant antibodies were produced all 19 substitutions at each of the 6 chosen positions (Table 3). The mutants were analyzed for binding to digoxin, digitoxin, digoxigenin and ouabain via ELISA as described in Example 1, resulting in the generation of a comprehensive data base of 456 relative affinity values. (Set 1=H:Tyr33; Set 2=H:Asn35; Set 3=H:Tyr50; Set 4=Trp100; Set 5=L:Val94; Set 6=Pro96).

TABLE 3

Relative affinity values of mutants for digitoxin, digoxin, ouabain and digitoxigenin as determined using ELISA

| Set | | Trp | Tyr | Phe | His | Ile | Val | Leu | Pro | Ala | Gly | Met |
|---|---|---|---|---|---|---|---|---|---|---|---|---|
| 1 | Digitoxin | 1.54 | 1.00 | 0.85 | 0.45 | 0 | 0.08 | 0 | 0 | 0.02 | 0.08 | 0.71 |
| 1 | Digoxin | 1.16 | 1.00 | 0.86 | 0.50 | 0.48 | 0.64 | 0.21 | 0.27 | 0.40 | 0.02 | 0.84 |
| 1 | Ouabain | 1.33 | 1.00 | 0.95 | 0.26 | 0 | 0 | 0.04 | 0.05 | 0.06 | 0.20 | 0.30 |
| 1 | Digitoxigenin | 1.34 | 1.00 | 0.98 | 0.90 | 0.10 | 0.13 | 0.04 | 0 | 0.04 | 0.01 | 0.35 |
| 2 | Digitoxin | 0.02 | 0.02 | 0.02 | 0.15 | 0.15 | 0.13 | 0.22 | 0.20 | 0.24 | 0.19 | 0.39 |
| 2 | Digoxin | 0.02 | 0.03 | 0.02 | 0.04 | 0.22 | 0.27 | 0.13 | 0.40 | 0.13 | 0.16 | 0.44 |
| 2 | Ouabain | 0.03 | 0.03 | 0.01 | 0.12 | 0.08 | 0.13 | 0.06 | 0.03 | 0.08 | 0.11 | 0.04 |
| 2 | Digitoxigenin | 0 | 0.01 | 0 | 0.03 | 0.03 | 0.01 | 0.03 | 0.02 | 0.03 | 0.04 | 0.03 |
| 3 | Digitoxin | 1.36 | 1.00 | 1.01 | 0.19 | 0.01 | 0.04 | 0.12 | 0 | 0.18 | 0.01 | 0.31 |
| 3 | Digoxin | 1.09 | 1.00 | 0.97 | 0.73 | 0.02 | 0.04 | 0.48 | 0 | 0.42 | 0.13 | 0.75 |
| 3 | Ouabain | 1.43 | 1.00 | 1.13 | 0.23 | 0.17 | 0.05 | 0.13 | 0.01 | 0.27 | 0.15 | 0.02 |
| 3 | Digitoxigenin | 1.20 | 1.00 | 0.94 | 0.36 | 0.09 | 0 | 0.01 | 0 | 0.06 | 0.05 | 0.15 |
| 4 | Digitoxin | 1.00 | 0.89 | 0.84 | 0.98 | 0.14 | 0.06 | 0.15 | 0.01 | 0.10 | 0.58 | 1.34 |
| 4 | Digoxin | 1.00 | 1.16 | 0.90 | 1.00 | 0.17 | 0.08 | 0.20 | 0.08 | 0.52 | 0.89 | 1.08 |
| 4 | Ouabain | 1.00 | 0.03 | 0.31 | 0.26 | 0.08 | 0.03 | 0.06 | 0 | 0 | 0 | 0.13 |
| 4 | Digitoxigenin | 1.00 | 0.53 | 0.40 | 0.89 | 0.05 | 0.01 | 0.06 | 0 | 0 | 0 | 0.86 |
| 5 | Digitoxin | 3.88 | 2.01 | 4.32 | 1.36 | 1.10 | 1.00 | 0.46 | 1.50 | 0.87 | 1.23 | 1.83 |
| 5 | Digoxin | 3.05 | 2.81 | 4.80 | 1.61 | 0.84 | 1.00 | 1.25 | 1.40 | 1.26 | 1.22 | 2.16 |
| 5 | Ouabain | 2.65 | 1.51 | 2.25 | 0.66 | 1.14 | 1.00 | 0.72 | 0.70 | 0.65 | 1.07 | 1.27 |
| 5 | Digitoxigenin | 1.95 | 1.96 | 3.65 | 1.03 | 1.16 | 1.00 | 0.86 | 0.66 | 0.88 | 0.67 | 2.00 |
| 6 | Digitoxin | 0 | 0.58 | 0.87 | 0.01 | 0.47 | 1.34 | 0.57 | 1.00 | 0.65 | 0.49 | 0.06 |
| 6 | Digoxin | 0 | 0.01 | 0.03 | 0 | 0.46 | 1.06 | 0.42 | 1.00 | 0.75 | 0.65 | 0.40 |
| 6 | Ouabain | 0 | 0.06 | 0.05 | 0 | 0 | 1.00 | 0.56 | 1.00 | 0.64 | 0.05 | 0.01 |
| 6 | Digitoxigenin | 0 | 0 | 0 | 0 | 0 | 1.15 | 0.01 | 1.00 | 0.74 | 0.11 | 0.01 |

| Set | | Cys | Thr | Ser | Gln | Asn | Glu | Asp | Lys | Arg | Stop |
|---|---|---|---|---|---|---|---|---|---|---|---|
| 1 | Digitoxin | 0.36 | 0.04 | 0 | 0 | 0 | 0 | 0 | 0.03 | 0 | 0 |
| 1 | Digoxin | 0.62 | 0.19 | 0.14 | 0.20 | 0.27 | 0.22 | 0 | 0.12 | 0.12 | 0 |
| 1 | Ouabain | 0.10 | 0.11 | 0.02 | 0 | 0 | 0.03 | 0 | 0 | 0.01 | 0 |
| 1 | Digitoxigenin | 0.12 | 0 | 0 | 0 | 0 | 0 | 0 | 0 | 0.03 | 0 |
| 2 | Digitoxin | 0.28 | 0.03 | 0.72 | 0.66 | 1.00 | 0.05 | 0.24 | 0.21 | 0.12 | 0 |
| 2 | Digoxin | 0.31 | 0.05 | 0.71 | 0.72 | 1.00 | 0.01 | 0.05 | 0.03 | 0.03 | 0 |
| 2 | Ouabain | 0.16 | 0.03 | 0.18 | 0.29 | 1.00 | 0.03 | 0.04 | 0.04 | 0.05 | 0 |
| 2 | Digitoxigenin | 0.01 | 0.01 | 0.31 | 0.42 | 1.00 | 0.01 | 0.02 | 0.02 | 0.02 | 0 |
| 3 | Digitoxin | 0.53 | 0 | 0.04 | 0 | 0 | 0 | 0 | 0 | 0.01 | 0 |
| 3 | Digoxin | 0.75 | 0.06 | 0.13 | 0.30 | 0.80 | 0.02 | 0 | 0 | 0 | 0 |
| 3 | Ouabain | 0.09 | 0.05 | 0.05 | 0.15 | 0.01 | 0.17 | 0.10 | 0.03 | 0.04 | 0 |
| 3 | Digitoxigenin | 0.17 | 0 | 0.03 | 0.10 | 0.27 | 0.07 | 0.05 | 0 | 0.01 | 0 |

TABLE 3-continued

Relative affinity values of mutants for digitoxin, digoxin, ouabain and digitoxigenin as determined using ELISA

| | | | | | | | | | | | |
|---|---|---|---|---|---|---|---|---|---|---|---|
| 4 | Digitoxin | 0.10 | 0.01 | 0.14 | 0.88 | 1.31 | 0 | 0.04 | 0.29 | 1.98 | 0 |
| 4 | Digoxin | 0.23 | 0.02 | 0.37 | 1.18 | 1.35 | 0.02 | 0.15 | 0.60 | 1.47 | 0 |
| 4 | Ouabain | 0.01 | 0 | 0 | 0.11 | 0.37 | 0 | 0.03 | 0 | 0.79 | 0 |
| 4 | Digitoxigenin | 0 | 0 | 0 | 0.43 | 0.98 | 0.05 | 0 | 0 | 1.44 | 0 |
| 5 | Digitoxin | 1.01 | 1.27 | 1.89 | 1.33 | 2.26 | 1.40 | 1.51 | 2.14 | 0.90 | 0 |
| 5 | Digoxin | 1.12 | 1.15 | 1.36 | 1.20 | 1.40 | 1.48 | 1.95 | 1.88 | 1.15 | 0 |
| 5 | Ouabain | 0.95 | 1.30 | 0.94 | 1.28 | 1.61 | 1.27 | 0.69 | 1.90 | 0.72 | 0 |
| 5 | Digitoxigenin | 0.99 | 1.07 | 1.07 | 1.25 | 1.80 | 0.98 | 0.29 | 2.13 | 0.81 | 0 |
| 6 | Digitoxin | 0.85 | 0.99 | 0.75 | 0 | 0.03 | 0 | 0 | 0 | 0.03 | 0 |
| 6 | Digoxin | 0.69 | 0.90 | 0.85 | 0 | 0.34 | 0 | 0 | 0 | 0.01 | 0 |
| 6 | Ouabain | 0.51 | 1.18 | 0.42 | 0 | 0 | 0 | 0 | 0 | 0 | 0 |
| 6 | Digitoxigenin | 0.69 | 0.99 | 0.64 | 0 | 0 | 0 | 0 | 0 | 0 | 0 |

As described in Example 1, the inventors' initial in vitro scanning saturation mutagenesis studies were performed on six residues that help define the interior of the anti-digoxin 26-10 antibody binding pocket. For each residue, the PCR mutagenesis and in vitro transcription/translation steps were carried out as described above in Example 1 in at least two independent runs to verify the reproducibility of the results. In addition, each ELISA, performed according to the procedure of Example 1, was run in duplicate. The reproducibility of the data was excellent, with absorbance values >20% of wild-type varying by no more than ±5% between studies (performed by different investigators). ELISA values lower than 20% of wild-type exhibited a greater degree of variability, presumably because of the lower signal to noise ratio. A low or absent ELISA signal was taken to mean that the off-rate was too fast for the scFv(Dig) mutants to remain bound to a significant extent during the incubations and washing steps, but does not necessarily imply complete loss of binding.

The ELISA results for the different mutants binding to digoxin and the three analogs (760 relative affinity values in all) are plotted as histograms in FIGS. 2A–2J. All absorbance values are normalized to the wild-type construct to allow for direct comparisons. It has been reported that the relative digoxin: digitoxin, digoxin: digoxigenin, and digoxin: ouabain affinities are 2:1, 1:1, and 42:1, respectively (Schildbach et al., 1993). Therefore, the relative ELISA values for the different cardiac glycosides in FIG. 2A, FIG. 2B, FIG. 2C, FIG. 2D, FIG. 2E, FIG. 2F, FIG. 2G, FIG. 2H, FIG. 2I and FIG. 2J must be scaled accordingly before any direct comparisons are made. The excellent agreement between the values for relative affinities and specificities for the different digoxin mutants in the literature (Short, et al., 1995; Schildbach et al., 1993; Schildbach et al., 1994; Near et al., 1993) underscores the validity of the inventors' methodology for the rapid generation and characterization of mutant antibodies. The data is useful in several ways. From the histograms it is possible to detect the residues that were most tolerant to substitution and, based on the types of substitutions tolerated, better understand what sorts of interactions are most important in antibody-antigen interaction. The mutagenisis assay was also able to uncover mutants with changed specificity and mutants with binding interactions of over four times that of the wild-type.

In particular, in this case, it was striking that in initial studies 87 out of the 114 substitutions resulted in significant (>5% of wild-type) recognition and binding to one or more of the digoxin analogs. This high degree of tolerance for a large number of amino acid substitutions is indicative of a high degree of plasticity in the antigen binding site. The residue most tolerant of substitution was L:Val94, where many amino acid substitutions increased ELISA absorbance values relative to the wild type. Increased absorbance values were especially apparent with large aromatic amino acid substitutions such as tryptophan and tyrosine, presumably due to increased Van der Waals contacts with the digoxin antigen. In contrast the three heavy chain aromatic residues that make substantial Van der Waals contacts with bound digoxin in the wild type tolerated only more conservative changes that did not greatly increase digoxin binding or change specificity; yet surprisingly positively charged residues such as lysine and arginine retained partial and full digoxin binding activity when substituted for H:Trp100. The residue least tolerant to substitution was H:Asn35, underscoring the importance of hydrogen bonding in this residues interaction with digoxin. The most active replacements for Asn were Gln and Ser, residues also capable of hydrogen bonding interactions. Single residue changes did not change the order of antigen specificity for digoxin relative to the larger oubain, but were capable of changing the order of specificity of the antibody for digoxigenin relative to digoxin. The difference between these two molecules lies in the sugar moiety which does not play a significant role in digoxin binding by the 26-10 antibody.

EXAMPLE 3

Further Elucidation of Specificity Determining Residues

In additional studies, values for the association and dissociation rate constants ($k_{on}$ and $k_{off}$, respectively) were measured using a BIAcore 1000 for the wild-type and 14 selected mutant scFv antibodies. These included 3 light chain mutants and 11 heavy chain mutants of varying affinities (Table 4). The selected scFv antibodies were expressed and purified following the procedure described by Burks and Iverson (1995). In each case, care was taken to insure that the kinetic values measured on the BIAcore are free of artifacts due to rebinding or avidity effects arising from multimeric scFvs. In particular, gel filtration HPLC was used to confirm that each scFv sample was ≧95% monomeric and a high flow rate (60 μl/min) as well as up to 1 mM soluble hapten was used in the dissociation buffer to prevent rebinding during the dissociation measurements. For some of the low affinity mutants ($K_a<10^6\ M^{-1}$) the values for $k_{on}$ could not be determined due to rapid dissociation and practical limits on the maximum concentration of mutant scFv that could be used. The values for $k_{on}$ of the mutants with higher overall affinity were obtained, all of which gave values near $10^6$ M$^{-1}$ s$^{-1}$. This value is very close to the maximum $k_{on}$ for the binding of a monomeric antibody (Schier et al., 1996; Foote and Eisen, 1995). On the other hand, as is expected for a set of related antibodies, the mutations mostly affect the values of $k_{off}$ (Wells, 1996).

phobicity coefficient for an amino acid residue j is calculated as the sum of the Tanford-Jones hydrophobicity coefficients of all the residues contained within an 8 Å sphere centered on the α carbon of residue j. The average value of the hydrophobicity distribution, obtained for each amino acid residue, is the mean hydrophobicity.

There was a significant correlation between the ELISA data of H:33 and the hydrophobicity coefficients derived

TABLE 4

Association and Dissociation rate constants
($k_{on}$ and $k_{off}$, respectively) for
the wild-type and 14 selected mutant scFv antibodies.

| | Digoxin | | | Digitoxin | | |
|---|---|---|---|---|---|---|
| | $k_{on}$ | $k_{off}$ | $K_a$ | $k_{on}$ | $k_{off}$ | $K_a$ |
| WT | $1.2 \times 10^8$ | $7.0 \times 10^{-4}$ | $1.7 \times 10^9$ | $1.0 \times 10^6$ | $1.3 \times 10^{-3}$ | $7.7 \times 10^8$ |
| LC96F | $1.0 \times 10^8$ | 2 | $5.0 \times 10^5$ | $1.18 \times 10^6$ | 0.014 | $8.4 \times 10^7$ |
| LC94Y | $1.2 \times 10^6$ | $5.2 \times 10^{-3}$ | $2.3 \times 10^8$ | $1.15 \times 10^6$ | $2.7 \times 10^{-3}$ | $4.3 \times 10^8$ |
| LC94F | $1.2 \times 10^6$ | $1.9 \times 10^{-3}$ | $6.3 \times 10^8$ | $1.3 \times 10^6$ | $1.3 \times 10^{-3}$ | $1.0 \times 10^9$ |
| HC9ST | $1.4 \times 10^6$ | $5.4 \times 10^{-3}$ | $2.6 \times 10^7$ | $1.0 \times 10^6$ | 0.11 | $9.0 \times 10^6$ |
| HC100R | $1.3 \times 10^6$ | $5.0 \times 10^{-3}$ | $2.6 \times 10^8$ | $9.3 \times 10^5$ | $8.2 \times 10^{-3}$ | $1.1 \times 10^8$ |
| HC100K | $9.4 \times 10^5$ | $8.0 \times 10^{-2}$ | $1.2 \times 10^7$ | | 0.09 | 0 |
| HC100H | $1.0 \times 10^6$ | $2.0 \times 10^{-3}$ | $5.0 \times 10^8$ | | $9.7 \times 10^{-3}$ | 0 |
| HC50F | $1.5 \times 10^6$ | $5.8 \times 10^{-4}$ | $2.6 \times 10^9$ | $9.6 \times 10^5$ | $1.7 \times 10^{-3}$ | $5.6 \times 10^8$ |
| HC50H | $9.7 \times 10^5$ | $4.0 \times 10^{-3}$ | $2.4 \times 10^8$ | $1.0 \times 10^6$ | 0.162 | $6.2 \times 10^6$ |
| HC50N | $1.1 \times 10^6$ | $9.0 \times 10^{-3}$ | $1.2 \times 10^8$ | $1.0 \times 10^6$ | 0.256 | $3.9 \times 10^6$ |
| HC50L | $1.1 \times 10^6$ | $4.5 \times 10^{-2}$ | $2.4 \times 10^7$ | | 0.208 | 0 |
| HC50D | | 0.17 | <1e7 | $8.0 \times 10^5$ | 2.1 | $3.8 \times 10^5$ |
| HC50G | $1.3 \times 10^6$ | 0.15 | $8.9 \times 10^6$ | | 1.38 | 0 |
| HC50A | $1.2 \times 10^6$ | 0.10 | $1.2 \times 10^7$ | | $9.6 \times 10^{-2}$ | 0 |

| | Ouabain | | | Digitoxigenin | | |
|---|---|---|---|---|---|---|
| | $k_{on}$ | koff | Ka | Kon | koff | Ka |
| WT | $1.0 \times 10^6$ | $1.5 \times 10^{-2}$ | $6.7 \times 10^7$ | $1.0 \times 10^6$ | $2.3 \times 10^{-2}$ | $4.3 \times 10^8$ |
| LC96F | | 0.3 | ND | ND | 0.169 | ND |
| LC94Y | $1.0 \times 10^6$ | $1.7 \times 10^{-2}$ | $6.0 \times 10^7$ | $1.1 \times 10^6$ | $1.8 \times 10^{-1}$ | $6.1 \times 10^7$ |
| LC94F | $1.0 \times 10^6$ | $1.0 \times 10^{-2}$ | $1.0 \times 10^8$ | $1.0 \times 10^6$ | $8.9 \times 10^{-2}$ | $1.1 \times 10^8$ |
| HC9ST | $1.0 \times 10^5$ | 0.12 | $6.7 \times 10^6$ | $7.0 \times 10^5$ | 1.00 | $7.0 \times 10^8$ |
| HC100R | $1.0 \times 10^6$ | 0.12 | $8.3 \times 10^6$ | $7.0 \times 10^5$ | $1.7 \times 10^{-1}$ | $4.2 \times 10^7$ |
| HC100K | | 0.60 | ND | $1.0 \times 10^6$ | 1.48 | $6.7 \times 10^6$ |
| HC100H | $1.0 \times 10^6$ | 0.09 | $1.1 \times 10^7$ | $1.0 \times 10^6$ | $9.7 \times 10^{-2}$ | $1.0 \times 10^8$ |
| HC50F | $1.0 \times 10^6$ | 0.013 | $7.9 \times 10^7$ | $1.0 \times 10^6$ | $2.2 \times 10^{-2}$ | $4.5 \times 10^8$ |
| HC50H | $1.0 \times 10^6$ | 1.6 | $6.2 \times 10^6$ | $1.0 \times 10^6$ | $3.5 \times 10^{-1}$ | $2.9 \times 10^7$ |
| HC50N | | 1.7 | ND | $1.1 \times 10^6$ | $6.4 \times 10^{-1}$ | $1.7 \times 10^7$ |
| HC50L | | 1.4 | ND | $1.1 \times 10^6$ | 1.13 | $1.0 \times 10^7$ |
| HC50D | | 0.14 | ND | $1.0 \times 10^6$ | 0.135 | $7.4 \times 10^6$ |
| HC50G | | 0.14 | ND | | 0.276 | ND |
| HC50A | | 0.217 | ND | $1.6 \times 10^6$ | 0.163 | $9.9 \times 10^6$ |

The relative ELISA values produced in the in vitro scanning saturation mutagenesis study were analyzed in the context of available amino acid indices. The goal of these analyses was to identify trends relating the observed ELISA signals to the various properties of the amino acid side chains as quantified in the various indices.

Hydrophobic effects often play a major role in antibody-antigen interactions (Davies and Cohen, 1996), especially when hydrophobic haptens, such as digoxin, are used. Over twenty different hydrophobic indices were evaluated with respect to the ELISA signals from the in vitro scanning saturation mutagenesis experiments. In no case was an overwhelming correlation seen. As a representative example, Cid et al. (1992) derived a hydrophobicity scale from 60 protein structures by considering the environment of each amino acid residue (Cid et al., 1992). They grouped the proteins into four structural classes defined by Levitt and Chothia: αα, ββ, α+β, and αβ, where Class ββ includes the immunoglobulins (Levitt and Chothia, 1976). The hydrofrom the ββ class of proteins (Cid et al., 1992). That is, replacing a less hydrophobic amino acid with a more hydrophobic amino acid generally results in a higher ELISA signal at residue H:33. The ELISA data at H:100b also correlates somewhat to the hydrophobicity indices of the amino acid substitutions), except for the bulky aromatic amino acids (Trp, Tyr, Phe, His) that are presumably too large. The correlation is much less compelling for residue H:50, while no pattern is identifiable for H:35, H:47, H:95, H:100, L:91, L:94 and L:96 even though these residues presumably make primarily hydrophobic contacts like H:33 and H: 100b.

Despite there being no correlation between the ELISA signals and hydrophobicity indices, one common trend for the five residues L:94, H:33, H:47, H:50 and H: 100 is that the substitutions with aromatic amino acids retain the ELISA signal, although in some cases, (especially H: 100), several non-aromatic residues of low hydrophobic index are also functional, albeit less active, substitutes.

Shape complementarity obviously influences the specificity and affinity of antibody-hapten interactions. Proper fit maximizes van der Waals interactions as well as the desolvation that likely dominates the energetics of the hydrophobic binding of the 26-10 antibody-digoxin interaction (Jeffery et al., 1993). Therefore, an index derived from calculated van der Waals volumes (Fauchere et al., 1988) was used to analyze the effects of residue size. According to the crystal structure of wild-type 26-10, residues at the bottom of the binding pocket make close contact to primarily the lactone and ring D portion of digoxin (Jeffery et al., 1993). Consistent with this notion, the effect of substitutions at residues H:35, H:95, H:100b, L:91 and L:96 on binding activity varies according to the change of van der Waals volume of amino acid with the exception of amino acid whose side chain may be too large to be accommodated within the binding pocket. In particular, the substitutions at the above mentioned sites resulted in binding similar to wild-type only when amino acids of similar or smaller size compared to wild-type were used. Residues L:91 and L:96 are particularly noteworthy, as no other parameter examined was as important as size at these positions. No correlation between van der Waals volume and binding activity could be observed for the other SDR residues.

The 26-10 crystal structure indicates hydrogen bonding involving H:Asn-35 and H:Ser-95 that could potentially play an important role in maintaining the structural integrity of the binding site. Plots of the number of potential hydrogen bonding donors on a given side chain versus the ELISA signals for the different residues indicated that there is indeed a correlation of hydrogen bonding ability with ELISA signal at H:35, and a slightly weaker correlation at H:95. No other residues displayed a correlation with hydrogen bonding ability.

The flexibility of the side chains of the amino acids (Bhaskaran and Ponnuswamy, 1988) was also investigated. In general, most of the residues already identified as showing a preference for aromatic replacements, namely H:33, H:47, H:50 and L:94, also show a preference for more rigid side chains. This, in fact, could well explain the aromatic, as opposed to simply hydrophobic preference, at these site. It is noteworthy that H:100, while generally preferring aromatic residues, also tolerates significant flexibility.

Discussion

The in vitro scanning saturation mutagenesis studies on the 26-10 antibody SDRs identified several single amino acid substitutions that displayed remarkable changes inspecificity for digoxin and related cardiac glycosides. For example, the L:Pro-96→Phe mutant has a striking preference, greater than two orders of magnitude, in favor of binding digitoxin over digoxin, digoxigenin or ouabain (Table 4). This effect is likely the result of an unfavorable steric interaction between the L:Pro-96→Phe phenyl ring side chain and the C12-OH group of digoxin, digoxigenin and ouabain that is absent in digitoxin. The H:Tyr-50→Asn, H:Trp-100→Lys and H:Trp-100→His mutants show a reciprocal specificity, namely a strong preference for binding to digoxin and digoxigenin compared to digitoxin. Computer models have thus far not indicated a rationale for these changes in specificity as especially the H:50 side chain is far from the C12 position of bound digoxin in the 26-10 structure.

Collectively, the data for all 190 mutants reveal several interesting trends. First, the 26-10 antibody binding pocket can be thought of as being relatively plastic, tolerating a large number of amino acid substitutions at the SDRs. Better than 86% of the 190 mutants in the 10 SDR positions retained binding affinities for digoxin of over $10^6$–$10^7$ $M^{-1}$. Second, no single site SDR mutant was found to have a higher overall affinity for digoxin than the wild-type 26-10. This remarkable finding indicates that the immune system, presumably due to fine-tuning through somatic hypermutation, has found an optimum solution to the binding of digoxin when one considers only single substitutions. Thus, in the context of the immune response, the binding site of 26-10 could well represent the endpoint of affinity maturation.

Another way to look at the data for the 190 mutants is that simultaneous mutations in multiple SDRs would be necessary in order to increase further digoxin binding for 26-10. It is highly unlikely that multiple mutations in SDRs would occur simultaneously in B lymphocytes undergoing affinity maturation. However, it is possible to select higher affinity antibodies with multiple mutations from combinatorial libraries in vitro. Using libraries displayed on the surface of E.coli and screened by FACS, a L:Val-94→Ile, L:Pro-96→Ala double mutant with 3-fold higher affinity than wild-type was identified. As shown here, neither of these mutations alone showed higher affinity. Similarly, Short et al. (1995) used phage display to isolate a H:Thr-30→Pro, H:Asp-31→Ser, H:Met-34→Tyr triple mutant with about four-fold higher affinity to digoxin relative to the wild-type. In this latter case none of the mutated residues were SDRs. By combining the L:Val-94→Ile, L:Pro-96→Ala, H:Thr-30→Pro, H:Asp-31→Ser, and H:Met-34→Tyr mutations an scFv antibody was generated that has a Ka for digoxin of around $1.2\times10^{10}$ $M^{-1}$, or 12-fold better than the wild-type scFv (GC, GG and BLI).

There are three factors that can potentially influence the level of ELISA signal observed for any given mutant in the present investigations; 1) differences in the amount of translated protein produced in the coupled transcription/translation reactions, 2) differences in the percentage of folded vs. unfolded protein for different mutants, and 3) relative affinities of the mutants produced.

Repeated ELISA measurements have verified that there is little variation ELISA experiments, averaging only ±5%, indicating that the assay itself is not a significant source of error. In addition, analysis of the in vitro translation products by Western blotting and by auroradiography demonstrated that the variability in the amount of scFv produced is less than ±10% for different mutants. Thus, the observed differences in the ELISA values do not arise from the variations in protein synthesis levels. Rather, the ELISA values must reflect primarily differences in binding affinity or folding yield. It is not possible a priori to distinguish between these two possibilities. Nonetheless there are two lines of data indicating that in most cases the ELISA signal reflects binding affinities: First, there is good agreement between the ELISA data and the relative affinities of several of the same 26-10 mutants reported in the literature (Schildbach et al., 1993; Short et al., 1995; Schildbach et al., 1994; Near et al., 1993). Second, there is also good agreement between the affinities and specificities measured for eleven of the fourteen selected mutants by SPR and the ELISA data obtained from in vitro scanning saturation mutagenesis (Table 4). It is noteworthy that this correlation was observed even though the mutants analyzed were intentionally chosen to cover a range of affinities.

For two L:94 mutants and one H:100 mutant the ELISA signal appeared to reflect differences in folding yield. For example, the in vitro scanning saturation mutagenesis ELISA data indicated that the L:Pro-94→Phe and L:Val-94→Tyr mutants should have higher affinity than wild-type 26-10, while the SPR measurements indicate they do not. Similarly, the H:Trp-100→Arg mutant displayed an ELISA signal that was equivalent to wild-type, even though measurements of the binding kinetics of the purified antibodies showed that this mutant has a somewhat lower affinity.

In vitro expression levels of these mutants were found to be similar to wild-type by Western blot analysis, so by process of elimination, an enhanced folding ability may be responsible for the reproducibly increased ELISA signal. Consistent with this notion, the L:Pro-94→Phe, L:Pro-94→Tyr and H:Trp-100→Arg mutants exhibited significantly higher yields of active protein than the other $scF_v$ constructs using the same refolding protocol (Burks and Iverson, 1995). In general, the speed and large amount of data generated by in vitro scanning saturation mutagenesis must be weighed against the inability to determine without further analysis whether a particular mutation is affecting data generated by in vitro scanning saturation mutagenesis must be weighed against the inability to determine without further analysis whether a particular mutation is affecting folding or binding affinity. The issue of folding efficiency is interesting in its own right from a protein engineering perspective: mutants that do not fold with a sufficiently high yield are of little interest for practical purposes whereas mutants exhibiting higher refolding yield than the wild-type antibody can be of considerable value for protein expression. Finally, it must be pointed out that differences in refolding yields do not interfere in any way with the identification of mutants with interesting new binding specificities.

Because of the considerations discussed above no simple correlation between the ELISA signal and Kd values can be found. However, comparison of the data discussed herein indicates certain guidelines. For example, no ELISA reading is observed for affinities that are more than three orders of magnitude below wild-type, that is lower than $10^6$ $M^{-1}$. However, a scaled ELISA reading of 0.4 corresponds to an affinity that is approximately two orders of magnitude below wild-type and a scaled reading of 0.7–0.8 corresponds to an affinity that is one order of magnitude lower than wild-type.

The ELISA data can also be used to evaluate the functional roles played by the different SDRs. A positive correlation between the ELISA data at a given residue and a quantified side chain attribute can be taken as evidence that the attribute in question is important for the functioning of the wild-type residue. Amino acid indices, intended to quantify the different side chain parameters of hydrophobicity, flexibility, hydrogen bonding ability and side chain volume, were used for correctional analyses (Tomi and Kanehisa, 1996).

Precise, quantitative correlation's between ELISA data and any one amino acid index are not necessarily to be expected here, as the properties of amino acid side chains are interrelated. In other words, it is reasonable to expect general trends indicating that more than one parameter, for example, both size and hydrogen bonding ability, are important at an SDR as opposed to a correlation to any single parameter. Consistent with this expectation, strong correlation's with single parameters were observed with the ELISA data for only two residues at the bottom of the binding pocket, namely L:91 and L:96, which correlated with side chain volume. However, several strong trends were identifiable for each of the other residues when more than one parameter was considered, and these multi-parameter trends have allowed the construction of a working model for the functional roles played by the 26-10 SDI's as described below.

Overall, side chain hydrophobicity showed a reasonably strong correlation with the ELISA data at H:33 and to a lesser extent H: 100b. The data for H: 100b was corrected for size limitations by ignoring extremely large side chains, which were inactive. The other SDI's showed no compelling relationship between ELISA signals and hydrophobicity. This observation transcends the exact hydrophobicity index used, as over twenty different hydrophobicity indices were investigated with results that were no better in terms of correlations than those presented herein using the index of Cid et al. (1992). The lack of general correlation for the other eight SDRs with hydrophobicity should not be used to argue against hydrophobic desolvation being the primary driving force for binding digoxin by 26-10. Rather, the lack of hydrophobic correlation was taken as evidence that other side chain parameters such as rigidity, hydrogen bonding ability and size must also be important and sometimes dominant.

A general trend was identified for the five residues L:94, H:33, 1:47, H:50 and H: 100, which all strongly preferred aromatic residues as replacements, especially Tyr and Trp. These aromatic groups form a "collar" and one side (H:47) of the binding pocket cavity that may have a structural role. Flexible hydrophobic residues at these positions might tend to "collapse" in aqueous solution, and perhaps the rigidity of the aromatic side chains are required to maintain an open structure, even in the absence of bound digoxin, analogous to the wood framing used to shore up an underground mine shaft. One piece of evidence to support this notion is that association rate constants of 26-10 mutants are all very close to $1\times10^6$ ($M^{-1}s^{-1}$) based on SPR data, indicating that the mutant binding pockets are "open" in the unbound state. In addition, the crystal structure of other antibodies complexed to hydrophobic haptens show a similar "hydrophobic collar" in their binding pocket (Wedemeyer et al., 1997). Thus, it appears that hydrophobicity coupled to the rigidity of the aromatic residues are important at key sites within 26-10 and perhaps other antibodies that have hydrophobic binding sites. Such a central role for these aromatic residues based on both rigidity and hydrophobicity likely explains the predominance of solvent exposed tyrosine and tryptophan in antibody binding pockets (Padlan, 1996).

Size appears to be a key parameter for the residues at the bottom of the binding pocket, namely H:100b, L:91 and L:96. In each case, ELISA signals increased with increasing residue size to a point, then fell off rapidly for the largest side chains. The binding pocket structure is likely robust enough at the bottom to prevent hydrophobic collapse so that considerable flexibility can be accommodated, thereby explaining why no correlation to rigidity was observed. Interestingly, most of the "specificity" mutants occurred at these bottom positions, ex. L:96. Perhaps it will turn out to be a general feature of antibodies that fewer structural rigidity constraints at the bottom of the pocket permit more fine tuning of the fit at these positions. Interestingly, as previously mentioned, mutants at H: 100b showed a correlation with hydrophobicity, but L:91 and L:96 displayed no recognizable hydrophobicity pattern. Thus, for these latter two residues, size appears to be the clearly predominant parameter.

Hydrogen bonding along with size appear to be the key parameters for residues H:35 and H:95. Presumably hydrogen bonding is required to maintain the structural integrity of the binding pocket. Interestingly, a largely hydrogen bonding structural role was previously predicted for both asparagine and serine based on the observation that they are overrepresented in antibody binding pockets, yet have a relatively small contact surface area with bound antigen (Padlan, 1996).

In vitro scanning saturation mutagenesis could prove particularly valuable for protein engineering studies, even with enzymes when coupled to a catalytic assay, as a rapid way of identifying mutants with interesting properties that can then be produced in large quantity and subjected to more detailed structural and functional characterization. In addition, in vitro scanning saturation mutagenesis represents a systematic new tool for exploring in vitro antibody affinity evolution, analogous to somatic hypermutation in vivo. Interesting single mutants can be used as a starting point for subsequent rounds of in vitro saturation mutagenesis at other sites, so that multiple mutations with synergistic effects on binding may be identified. This same sequential mutation approach should be useful with other types of proteins, so that attributes such as expression level, folding ability, catalytic rate or substrate specificity could be modulated in a systematic way.

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

H. References

The following references, to the extent that they provide exemplary procedural or other details supplementary to those set forth herein, are specfically incorporated herein by reference:

Barbas et al., *Proc. Natl. Acad. Sci. USA*, 88:7978–7982, 1991.
Barbas et al., *Proc. Natl. Acad. Sci. USA*, 89:4457–4461, 1992.
Bhaskaran and Ponnuswamy, *Int. J. Peptide Protein Res.* 32, 241–255, 1988.
Blackburn et al., *Clin. Chem.*, 37:1534–1539, 1991.
Braden et al., *FASEB Journal*, 9:9–16, 1995.
Braisted and Wells, *Proc. Nat'l Acad. Sci. USA*, 93:5688–5692, 1996.
Brand et al., *J Immunol*, 153(7):3070–8, 1994.
Brand et al., *J lmmunol*, 152(8):4120–4128, 1994.
Breyer and Sauer, *J Biol Chem*, 264(22):13355–60, 1989.
Brown et al., *J. Immunology*, 156:3285–3291, 1996.
Bruce et al., *Rapid Commun Mass Spectrom*, 9(8):644–50, 1995.
Brummell et al., *Biochemistry*, 32:1180–1187, 1993.
Brutlag et al., *Comput Appl Biosci*, 6(3):237–45, 1990.
Burbaum et al., *Proteins*, 7(2):99–111, 1990.
Burks and Iverson, *Biotechnol. Prog.*, 11:112–114, 1995.
Burks et al., *Proc. Natl. Acad. Sci. USA*, 94:412–417, 1997.
Burton and Barbas, *Adv. Immunol.*, 3rd, 57:191–280, 1994.
Campbell, in: *Monoclonal Antibody Technology, Laboratory Techniques in Biochemistry and Molecular Biology*, Vol. 13, Burden & Von Knippenberg, Amsterdam, Elseview, pp. 75–83, 1984.
Chen et al., *EMBO J.*, 14:2784–2794, 1995.
Chou and Fasman, *Biochemistry*, 13(2):211–222, 1974b.
Chou and Fasman, *Ann. Rev. Biochem.*, 47:251–276, 1978b.
Chou and Fasman, *Biophys. J.*, 26:367–384. 1979.
Chou and Fasman, *Biochemistry*, 13(2):222–245, 1974a.
Chou and Fasman, *Adv. Enzymol. Relat. Areas Mol. Biol.*, 47:45–148, 1978a.
Cid et al. *Protein Engineering*, 5:373–375. 1992.
Clackson and Wells, *Science*, 267(5196):383–6, 1995.
Cunningham et al., *Science*, 243(4896):1330–1336, 1989.
Davey et al., EPA No. 329 822
Davidson and Sauer, *Proc Natl Acad Sci*, 91(6):2146–50, 1994.
Davidson et al., *Nat Struct Biol*, 2 (10) p856–64, 1995.
Davies and Cohen, *Proc. Nat. Acad. Sci., USA* 93, 7–12.1996.
EPA No. 320 308
Fauchere et al., *Int. J. Peptide Protein Res.*, 32:269–278 1988.
Fetrow and Bryant, *Biotechnology*, 11(4):479–84, 1993.
Foote and Eisen, *Proc. Natl. Acad Sci. USA*, Vol. 92, 1254–1256. 1995.
Francisco et al., *Proc. Nat'l Acad. Sci. USA*, 90:10444–10448, 1993.
Freier et al., *J Med Chem*, 38(2):344–52, 1995.
Friguet et al., *J Immunol Methods.*, 158(2):243–249, 1993.
Frohman, In: *PCR Protocols: A Guide to Methods and Applications*, Academic Press, N.Y., 1990.
GB Application No. 2 202 328
Gefter et al., *Somatic Cell Genet.*, 3:231–236, 1977.
Goding, in: *Monoclonal Antibodies: Principles and Practice*, 2nd Ed., Orlando, Fla., Academic Press pp. 60–61, 65–66, 71–74, 1986.
Harlow and Lane, *Antibodies: A Laboratory Manual*, Cold Spring Harbor Lab. Press, New York, 1988.
Harrison et al., *Methods Enzymol*, 267:109–115, 1996.
Higuchi et al., *Nucleic Acid Res.*, 16:7351–7367, 1988.
Hilton et al., *J. Biol. Chem.*, 271:4699–4708, 1996.
Ho et al., *Gene*, 77:51–59, 1989.
Holmes et al., *Biopolymers*, 37(3):199–211, 1995.
Horton and Pease, (M. J. McPherson, ed), 217–247, Oxford University Press, New York, N.Y., 1991.
Huston et al., *Methods in Enzymology*, "Molecular Design and Modeling: Concepts and Applications," Abelson & Simon, Academic Press, Inc., San Diego, pp. 46–99, 1991.
Huston et al., *Proc. Nat'l Acad. Sci. USA*, 85:5870–5883, 1988.
Innis et al., *PCR Protocols*, Academic Press, Inc., San Diego Calif., 1990.
Ito et al., *J. Biol. Chem.*, 268:16639–16647, 1993.
Iverson et al., *Cold Spring Harbor Symposia on Quantitative Biology*, 54:273–281, 1989.
Jackson et al., *J. Immunol.*, 154:3310–3319, 1995.
Jameson and Wolf, *Comput. Appl. Biosci.*, 4(1):181–186, 1988.
Jeffery et al., *Proc. Nat'l Acad. Sci. USA*, 90:10310–10314, 1993.
Kabat et al., In: *Sequences of Proteins of Immunological Interest*, U.S. Dept. of Health and Human Services, U.S. Government Printing Office, 1987.
Karlson et al., *J. Immunol. Methods*, 145, 229–240. 1991.
Kohler and Milstein, *Eur. J. Immunol.*, 6:511–519, 1976.
Kohler and Milstein, *Nature*, 256:495–497, 1975.
Krieg and Melton, *Methods Enzymol*, 155 p397–415, 1987.
Kudlicki et al., *J. Biol. Chem.*, 269:16549–16553, 1994.
Kwoh et al., *Proc. Nat. Acad. Sci. USA*, 86:1173–1177, 1989.

Kyte and Doolittle, *J. Mol. Biol.* 157, 105–132,1982.
Laemmli, U. K., *Nature*, 227:680–685, 1970.
Levitt and Chothia, *Nature*, 261(5561):552–558, 1976.
Lillehoj and Malik, *Adv Appl Microbiol.*, 38:149–209, 1993.
Makrides, S. C., *Microbiol. Rev.*, 60(3):512–538, 1996.
Maniatis et al., *Molecular Cloning: A Laboratory Manual*, Cold Springs Harbor Laboratories, Cold Springs Harbor, N.Y., 1982.
Maniatis et al., *Molecular Cloning: A Laboratory Manual*, Cold Springs Harbor Laboratories, Cold Springs Harbor, N.Y., 1989.
Martin et al., *J Med Chem.*, 38(9): 1431–1436, 1995.
Matthews, *Adv. Prot. Chem.*, 46:249–278, 1995.
Miller et al., PCT Application WO 89/06700
Morrison, S. L., *Annu Rev Immunol*, 10:239–65, 1992.
Mudgett-Hunter et al., *J. Immnol.*, 129:1165–1172, 1982.
Myszka et al., *Biophysical Chemistry*, 64:127–137, 1997.
Near et al., *Mol. Immun.*, 30:369–377, 1993.
Nicholls, et al., *J Biol Chem.*, 268(7):5302–5308, 1993.
Nieba et al., *Anal. Biochem.*, 234:155–165, 1996.
O'Hara, et al., *Proc. Nat'l Acad. Sci. USA*, 86:5673–5677, 1989.
Oddie et al., *Anal. Biochem.* 244, 301–311, 1997.
Ohlmeyer et al., *Proc Natl Acad Sci*, 90 (23), 1993.
Pace et al., *Protein Science*, 4:24 11–2423, 1995.
Padlan, *Advances in Protein Chemistry.*, 49:57–133, 1996.
Parker, C. W., In *Handbook of Experimental Immunology*, 3rd ed, (Weir DM ed), Blackwell Scientific, Oxford, 1978.
PCT Application No. PCT/US87/00880
PCT Application No. PCT/US89/01025, *Science*, 253: (5026):1408–11, 1991.
Pelham et al., *Eur J Biochem.* 67(1): 247–256, 1976.
Reidhaar-Olson and Sauer R T, *Science*, 241(4861):53–7, 1988.
Reidhaar-Olson and Sauer, *Proteins*, 7(4):306–16, 1990.
Roberts et al., *Br J Haematol.* 25(2):203–206, 1973.
Schier et al., *J. Mol. Biol.* 263, 551–567, 1996.
Schildbach et al., *J. of Biol. Chem.*, 268:21739–21747, 1993b.
Schildbach et al., *Protein Science*, 2:206–214, 1993a
Schildbach et al., *Protein Science*, 3:737–749, 1994.
Short et al., *J. Biol. Chem.*, 270:28541–28550, 1995.
Smith et al., *Biochemistry*, 9:331–337, 1970.
Studier et al., *Methods Enzymol*, 185:60–89, 1990.
Tomii and Kanehisa, *Protein Engineering*, 9:27–36, 1996.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,554,101
U.S. Pat. No. 4,683,195
U.S. Pat. No. 4,683,202
U.S. Pat. No. 4,800,159
U.S. Pat. No. 4,883,750
U.S. Pat. No. 5,221,605
U.S. Pat. No. 5,238,808
Walker et al., *Proc. Nat'l Acad. Sci. USA*, 89:392–396, 1992.
Warren et al., *Biochemistry*, 35:8855–8862, 1996.
Wedemeyer et al., *Science*, 276, 1665–1669 1997.
Weinberger et al., *Science*, 228(4700):740–2, 1985.
Wells and de Vos, *Annu Rev Biophys Biomol Struct*, 22:329–51, 1993.
Wells, J. A., *Proc. Nat'l Acad. Sci. USA*, 93:1–6, 1996.
Wolf et al., *Comput. Appl. Biosci.*, 4(1):187–191, 1988.
Wong et al., *J. Immunol.*, 154:3351–3358, 1995.
Wu et al., *Genomics*, 4:560–569, 1989.
Yang et al., *Proc Natl Acad Sci.*, 77(12):7029–7033, 1980.
Yelton et al., *J. Immunol.*, 155:1994–2004, 1995.
Zeder-Lutz et al., *Anal. Biochem.*, 246:123–132. 1997.
Zubay et al., *Proc Natl Acad Sci*, 66(1):104–10, 1970.

---

What is claimed:

1. A method of identifying an antibody variant comprising the steps of:
    a) providing a DNA segment encoding a antibody, or antigen-binding fragment thereof;
    b) providing a set of primers that encode all nineteen naturally-occurring amino acid variants at a single residue of said antibody or antigen-binding fragment thereof;
    c) performing PCR reactions on said DNA segment, using said set of primers, to generate a set of variant DNA segments encoding nineteen amino acid substitution variants at said single residue of said antibody or antigen binding fragment thereof;
    d) expressing each of said substitution variants using in vitro transcription/translation;
    e) identifying said antibody variant by increased antigen binding specificity.

2. The method of claim 1, wherein said transcription/translation employs a prokaryotic expression system.

3. The method of claim 1, wherein said gene is under the transcriptional control of a phage promoter.

4. The method of claim 3, wherein said promoter is T7, trc, tac, lpp-lac, trp, tet, lac, PBAD, phoA or $P_L$.

5. The method of claim 1, wherein said antigen binding activity is assessed by ELISA.

6. The method of claim 1, wherein said DNA segment encodes a single-chain antibody.

7. The method of claim 1, wherein said primers are between about 10 and about 50 bases in length.

8. The method of claim 1, wherein said antibody is a catalytic antibody, and said antibody variant further is identified by means of enzymatic activity.

9. A method of identifying an antibody variant comprising the steps of:
    a) providing a DNA segment encoding a antibody, or antigen-binding fragment thereof;
    b) providing a set of primers that encode all naturally occurring nineteen amino acid variants at a single residue of said antibody or antigen-binding fragment thereof;
    c) performing PCR reactions on said DNA segment, using said set of primers, to generate a set of variant DNA segments encoding nineteen amino acid substitution variants at said single residue of said antibody or antigen binding fragments thereof;
    d) repeating steps b and c at a second residue of said antibody or antigen binding fragment thereof;
    e) expressing each of said substitution variants using in vitro transcription/translation; and
    f) identifying said antibody variant by increased antigen binding affinity.

10. The method of claim 9, wherein said transcription/translation employs a prokaryotic expression system.

11. The method of claim 9, wherein said gene is under the transcriptional control of a phage promoter.

12. The method of claim 11, wherein said promoter is T7, trc, tac, lpp-lac, trp, tet, lac, PBAD, phoA or $P_L$.

13. The method of claim 9, wherein said antigen binding activity is assessed by ELISA.

14. The method of claim 9, wherein said DNA segment encodes a single-chain antibody.

15. The method of claim 9 wherein primers are between about 10 and about 50 bases in length.

16. The method of claim 9 wherein said antibody variant or antigen binding fragment thereof exhibits a lesser degree of cross-reactivity with related antigen species than does said antibody.

17. The method of claim 9, wherein said antibody is a catalytic antibody, and said antibody variant further is defined by means of enzymatic activity.

18. The method of claim 9, wherein steps b and c are repeated a second time.

19. The method of claim 18, wherein steps b and c are repeated a third time.

20. The method of claim 19, wherein steps b and c are repeated a fourth time.

21. The method of claim 20, wherein steps b and c are repeated a fifth time.

* * * * *

UNITED STATES PATENT AND TRADEMARK OFFICE
CERTIFICATE OF CORRECTION

| | |
|---|---|
| PATENT NO. | : 6,180,341 B1 |
| APPLICATION NO. | : 09/070408 |
| DATED | : January 30, 2001 |
| INVENTOR(S) | : Brent L. Iverson et al. |

It is certified that error appears in the above-identified patent and that said Letters Patent is hereby corrected as shown below:

In column 1, line 9, insert
--This invention was made with government support under grant number 9412502 awarded by the National Science Foundation. The government has certain rights in the invention.--.

Signed and Sealed this

Twenty-second Day of December, 2009

David J. Kappos
*Director of the United States Patent and Trademark Office*